(12) United States Patent
Grant et al.

(10) Patent No.: US 12,351,589 B2
(45) Date of Patent: Jul. 8, 2025

(54) REDOX ACTIVE MATERIALS, PROCESSES AND USES THEREOF

(71) Applicant: KASIS ENVIRONMENTAL LTD., Moncton (CA)

(72) Inventors: Andrew S. Grant, Sackville (CA); Travis Osmond, Moncton (CA)

(73) Assignee: KASIS ENVIRONMENTAL LTD., Moncton (CA)

( * ) Notice: Subject to any disclaimer, the term of this patent is extended or adjusted under 35 U.S.C. 154(b) by 0 days.

(21) Appl. No.: 18/391,693

(22) Filed: Dec. 21, 2023

(65) Prior Publication Data

US 2024/0199646 A1    Jun. 20, 2024

Related U.S. Application Data

(63) Continuation of application No. 17/766,496, filed as application No. PCT/CA2020/051319 on Oct. 2, 2020, now Pat. No. 11,851,444.

(60) Provisional application No. 62/910,525, filed on Oct. 4, 2019.

(51) Int. Cl.
  *C07D 513/08*    (2006.01)
  *B01J 20/22*     (2006.01)
  *H01M 8/18*      (2006.01)

(52) U.S. Cl.
  CPC ............ *C07D 513/08* (2013.01); *B01J 20/22* (2013.01); *H01M 8/188* (2013.01)

(58) Field of Classification Search
  CPC .................................................. C07D 513/08
  See application file for complete search history.

(56) References Cited

U.S. PATENT DOCUMENTS

| 6,177,017 | B1 | 1/2001 | Ward |
| 11,851,444 | B2 | 12/2023 | Grant et al. |
| 2022/0411441 | A1 | 12/2022 | Grant et al. |

FOREIGN PATENT DOCUMENTS

| EP | 0826784 | 3/1998 |
| WO | 2019012278 | 1/2019 |

OTHER PUBLICATIONS

Haberl et al., Uber 2,5-Endimino-1,4-dithiane VIII. Mitteilung uber α-Oxomercaptane, Monatshefte fuer Chemie vol. 88, pp. 996-1003 (Year: 1957).*

Barry et al., "Anticancer Agents. IV.la,b The Antitumor Activity of Some 1,4- and 1,5-(Bisthiosemicarbazones) and of Related Heterocycles", Journal of Medical Chemistry, 1970, vol. 13, No. 3, pp. 421-427. (The year of publication is sufficiently earlier than the effective U.S. filing date so that the particular month of publication is not an issue).

Ramsaywack et al., "Synthesis and Surface Investigations of N-Substituted 2,5-Dithio-7-azabicyclo[2.2.1]heptanes on Gold Surfaces", J. Phys. Chem. C 2012, 116, 7886-7896. (The year of publication is sufficiently earlier than the effective U.S. filing date so that the particular month of publication is not an issue).

Saiz et al., "Enantioselective synthesis of new oxazolidinylthiazolidines as enzyme inhibitors", Tetrahedron: Asymetry 28 (2017) 110-117. (The year of publication is sufficiently earlier than the effective U.S. filing date so that the particular month of publication is not an issue).

Vairoletti et al., "Synthesis of bicyclic 1,4-thiazepines as novel anti-Trypanosoma brucei brucei agents", Med. Chem. Commun. Jun. 2019, 10, 1481.

Zhdanko et al., "One-step synthesis of N-acetylcysteine and glutathione derivatives using the Ugi reaction", Tetrahedron 65 (Apr. 2009) 4692-4702.

Hainey et al., "Oligoamine-functionalised poly(glycidyl) methacrylate-ethylegeglycol dimethacrylate) resins as moderate base extractants for gold from cyanide solutions", Reactive & Functional Polymers 43 (Feb. 2000) 195-210.

Sanchez-Loredo et al., "Preparation of gold powders by means of redox-active extractive systems", Materials Chemistry and Physics 76 (Sep. 2002) 279-284.

Alkhabbaz et al., "Guanidinylated poly(allylamine) supported on mesoporous silica for CO2 capture from flue gas", Fuel 121 (2014) 79-85. (The year of publication is sufficiently earlier than the effective U.S. filing date so that the particular month of publication is not an issue).

Fu et al., "Removal of heavy metal ions from wastewaters: A review", Journal of Environmental Management 92 (2011) 407-418. (The year of publication is sufficiently earlier than the effective U.S. filing date so that the particular month of publication is not an issue).

Goswami et al., "Silical gel functionalized with resacetophenone: synthesis of a new chelating matrix and its application as metal ion collector for their flame atomic absorption spectrometric determination", Analytical Chimica Acta 454 (2002) 229-240. (The year of publication is sufficiently earlier than the effective U.S. filing date so that the particular month of publication is not an issue).

* cited by examiner

*Primary Examiner* — Brenda L Coleman
(74) *Attorney, Agent, or Firm* — SMART & BIGGAR LP

(57) ABSTRACT

The present disclosure relates to a redox active materials comprising at least one 2,5-dithio-7-azabicyclo[2.2.1]heptane unit connected to a surface thereof, as well as processes for making said redox active materials. The present disclosure relates to a method for recovering a metal, comprising reacting a metal in oxidized state with the redox active material herein disclosed. The present disclosure relates to uses of redox active materials herein disclosed in sensors, electronic materials and for extracting various metals.

14 Claims, 18 Drawing Sheets

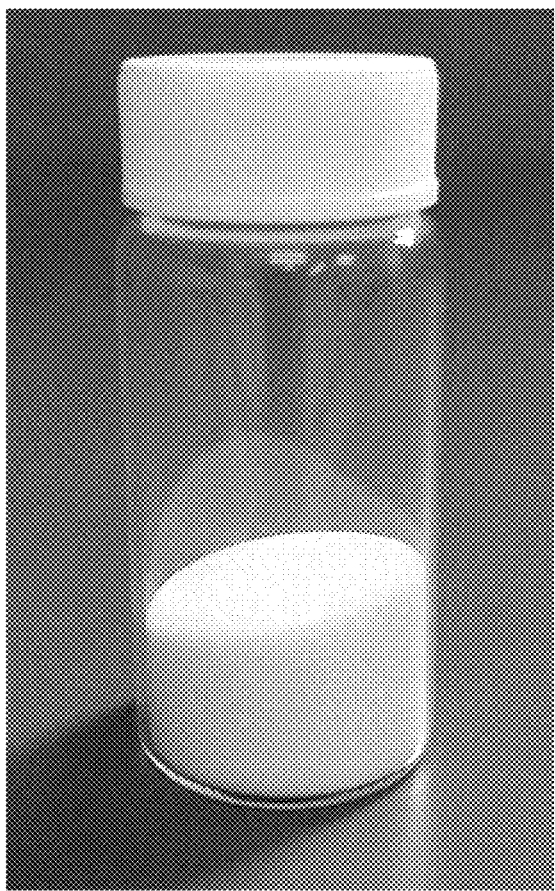
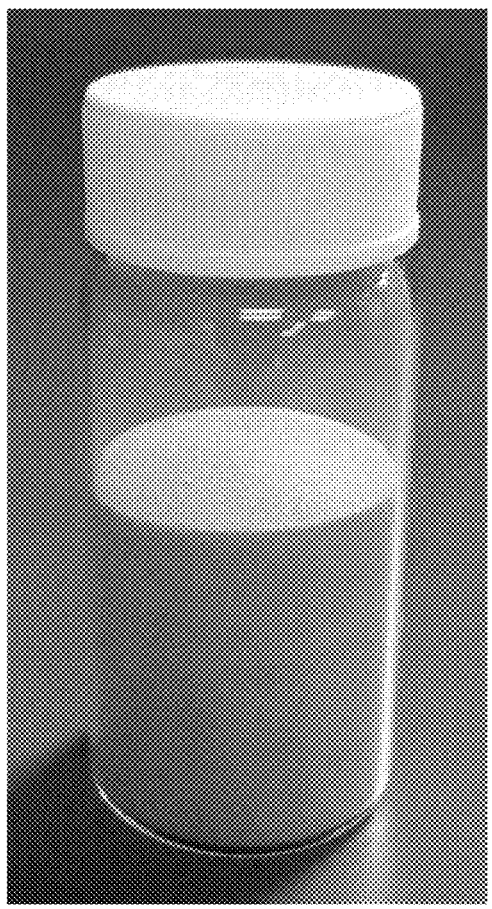
Fig. 2A                                   Fig. 2B

REDOX ACTIVE MATERIALS, PROCESSES AND USES THEREOF

CROSS-REFERENCE TO RELATED APPLICATIONS

The present disclosure is a continuation application of U.S. Ser. No. 17/766,496, filed on Apr. 4, 2022, that is a 35 USC 371 national stage entry of PCT/CA2020/051319, filed on Oct. 2, 2020, and which claims the benefit of priority from U.S. patent application No. 62/910,525, filed Oct. 4, 2019. These documents are hereby incorporated by reference in their entirety.

FIELD

The present disclosure relates to a new class of functional materials that exhibit redox properties, processes to prepare such materials, and uses thereof, and more particularly to materials incorporating one or more 2,5-dithio-7-azabicyclo[2.2.1]heptane units that are substituted or unsubstituted.

BACKGROUND

Materials that bind metals and in particular precious metals from solution are of considerable value. Materials that have previously been examined for these purposes include natural materials such as cellulose, chitin, chitosan and zeolites (F. Fu, Q Wang, Journal of Environmental Management 92 (2011) 407e418). Other materials have been made through the chemical modification of different forms of cellulose, chitin, chitosan, zeolites and silica gel. Modifications generally involve covalent attachment of thiols, thioethers, amines, polyamines, imidazole groups, amides. Synthetic, polymeric materials have also been examined. Regardless of the material, the result is that these materials and modified materials bind metals through a chelation effect or an electrostatic attraction.

Materials that react selectively with metals such as precious metals in their oxidized form, $M^{n+}$ in aqueous solution, reducing them to the zero-oxidation state, are highly desirable.

Known precious metal extraction processes are costly and environmentally polluting (e.g. cyanide). There is a need for improved processes for recovering precious metals, for example processes that do not require the use of toxic chemicals such as cyanide.

SUMMARY OF THE DISCLOSURE

A first aspect disclosed herein relates to a redox active material having Formula I:

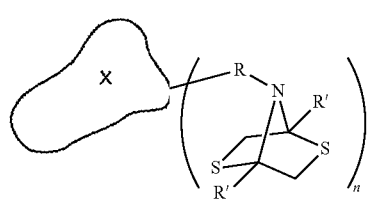

(I)

wherein X is a solid phase carrier; R is a linker or a chemical bond; n is any integer greater than 0; and R'
is chosen from hydrogen, $C_1$-$C_{20}$ alkyl, $C_3$-$C_8$ cycloalkyl, $C_6$-$C_{12}$ aryl, $C_1$-$C_{12}$ heteroaryl, $C_1$-$C_{12}$ heterocyclyl and $C_6$-$C_{20}$ aralkyl, said alkyl, cycloalkyl, heteroaryl and heterocyclyl being unsubstituted or substituted with at least one substituent chosen from a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl and $C_1$-$C_6$ hydroxyalkyl, an enantiomer thereof, a mixture of said redox active material having Formula I and said enantiomer thereof, diastereoisomers thereof, stereoisomers thereof and epimers thereof.

Another aspect disclosed herein is a redox active material comprising a solid phase carrier having at least one substituted or unsubstituted 2,5-dithio-7-azabicyclo[2.2.1]heptane unit connected to a surface thereof.

A further aspect relates to a process for preparing a redox active material, comprising
reacting a functionalized solid phase carrier having at least one primary amine bound at a surface thereof with a substituted or unsubstituted 2,5-dihydroxy-1,4-dithiane to obtain said redox active material.

Also provided herein in a further aspect is a process for preparing a redox active material, comprising
functionalizing a solid phase carrier; and
reacting said functionalized solid phase carrier with a substituted or unsubstituted 2,5-dihydroxy-1,4-dithiane to obtain said redox active material.

Another aspect relates to a process for preparing a redox active material, comprising
reacting together a solid phase carrier, a primary amino linker and a substituted or unsubstituted 2,5-dihydroxy-1,4-dithiane to obtain said redox active material.

In another aspect, there is provided a process for preparing a redox active material, comprising
connecting to a surface of a solid phase carrier at least one substituted or unsubstituted 2,5-dithio-7-azabicyclo[2.2.1]heptane unit to obtain said redox active material.

A further aspect herein disclosed relates to a process for preparing a redox active material, comprising
connecting to a surface of a solid phase carrier at least one substituted or unsubstituted 7-(prop-3-triethoxysilane)-(2,5-dithia-7-aza-bicyclo[2.2.1]heptane unit to obtain said redox active material.

A further aspect herein disclosed relates to a process for preparing a redox active material, comprising polymerizing a 2,5-dithio-7-azabicyclo[2.2.1]heptane modified monomer by either anionic, cationic or radical polymerization to obtain said redox active material. In some embodiments, the process relates to olefin polymerization and poly-condensation polymerization.

A further aspect herein disclosed relates to a process for preparing a redox active material, copolymerizing a 2,5-dithio-7-azabicyclo[2.2.1]heptane-containing monomer with a co-monomer in a ratio from 1:1 to 1:1000 (monomer: co-monomer), optionally in a ratio from 1:1 to 1:100, to obtain said redox active material. In some embodiments, the process relates to olefin polymerization—copolymerization and poly-condensation co-polymerization.

A further aspect herein disclosed relates to a process for preparing a redox active polyester comprising polymerizing or polycondensating a 2,5-dithio-7-azabicyclo[2.2.1]heptane-containing monomer with a linker agent diol (condensing agent) to obtain said redox active polyester material.

A further aspect herein disclosed relates to a process for preparing a redox active polyester material comprising copolymerizing or cocondensating a 2,5-dithio-7-azabicyclo[2.2.1]heptane-containing monomer with a co-monomer in a ratio from 1:1 to 1:1000 (monomer:co-monomer), optionally in a ratio from 1:1 to 1:100 to obtain said redox active polyester material.

A further aspect herein disclosed relates to a process for preparing a redox active polyamide material comprising polymerizing (or polycondensating) a 2,5-dithio-7-azabicyclo[2.2.1]heptane-containing monomer with a linker agent diamine (condensing agent) to obtain said redox active polyamide material.

A further aspect herein disclosed relates to a process for preparing a redox active polyamide material comprising copolymerizing (or cocondensating) a 2,5-dithio-7-azabicyclo[2.2.1]heptane-containing monomer with a co-monomer in a ratio from 1:1 to 1:1000 (monomer:co-monomer), optionally in a ratio from 1:1 to 1:100, to obtain said redox active polyamide material.

Also provided in the present disclosure is a redox active material obtained according to any one of the processes described herein.

In another aspect, there is provided a method for recovering a metal, comprising:
reacting a metal in an oxidized state with the redox active material herein disclosed or the redox active material obtained according to the process herein disclosed so as to reduce the metal; and
obtaining a reduced metal that is adsorbed to the redox active material.

In yet another aspect, there is provided a use of the redox active material disclosed herein or of the redox active material obtained according to the process disclosed herein as an anion exchange material, a halogen scavenger agent, a water filtration agent, a halogen filter agent, an air, water and/or petroleum detector agent, in dialysis or in drug synthesis.

The presently disclosed materials may be used for example in filters, sensors, electronic materials including semiconductors, electronic storage devices, and optics. The materials may also have applications for example in halogen adsorption, cyanide-free gold mining, precious metal electronic waste (e-waste) recovery, recovery of precious metals from cross-coupling chemical processes, water and air filtration and purification, as anion exchange materials, and engineered redox materials for use in electronic applications such as batteries, as well as toxic and heavy metal adsorption.

Also, when the redox active materials are oxidized (lose an electron), either deliberately or as a result of a process requiring the reducing materials to be oxidized, these materials produce an additional class of cationic, anion exchangeable, oxidizing materials, with their own unique properties and applications.

Another aspect herein disclosed relates to a compound of formula:

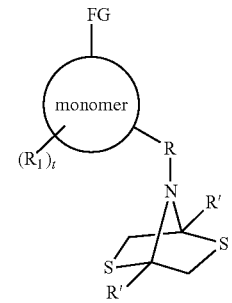

XVII

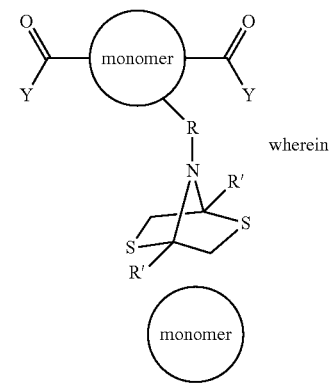

XVIII wherein

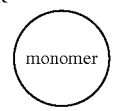

is chosen from $C_1$-$C_{20}$ alkyl, $C_3$-$C_8$ cycloalkyl, $C_6$-$C_{12}$ aryl, $C_1$-$C_{12}$ heteroaryl, $C_1$-$C_{12}$ heterocyclyl and $C_6$-$C_{20}$ aralkyl, and wherein R, R', are as previously defined; $R_1$ is chosen from hydrogen, $C_1$-$C_{20}$ alkyl, $C_3$-$C_8$ cycloalkyl, $C_1$-$C_{12}$ heteroaryl, $C_1$-$C_{12}$ heterocyclyl and $C_6$-$C_{20}$ aralkyl, and t is an integer from 1 to 4 such that the $R_1$ groups (if more than one) could be the same or different, attached to any position around the ring; FG is a polymerizable functional group such as vinyl or ethynyl, and Y is hydroxy, methoxy, ethoxy, 2,2,2-trichloroethoxy or benzyloxy, an enantiomer thereof, a mixture of compound having said formula and said enantiomer, diastereoisomers thereof, stereoisomers thereof and epimers thereof.

Yet another aspect herein disclosed relates to a compound of any one of formulas I to XVI.

In another aspect, the present disclosure includes a redox-active material of the present disclosure or a redox-active material obtained from a process of the present disclosure for use in a medical application.

In another aspect, the present disclosure includes a redox-active material of the present disclosure or a redox-active material obtained from a process of the present disclosure for use in diagnosis of a disease or condition.

In another aspect, the present disclosure includes a use of a redox-active material of the present disclosure or a redox-active material obtained from a process of the present disclosure in a medical application.

In another aspect, the present disclosure includes a use of a redox-active material of the present disclosure or a redox-active material obtained from a process of the present disclosure in diagnosis of a disease or condition.

In another aspect, the present disclosure includes a peptide, protein or polymer labelled with one or more substituted or unsubstituted 2,5-dithio-7-azabicyclo[2.2.1]heptane units for use in a medical application.

In another aspect, the present disclosure includes a peptide, protein or polymer labelled with one or more substituted or unsubstituted 2,5-dithio-7-azabicyclo[2.2.1]heptane units for use in diagnosis of a disease or condition.

In another aspect, the present disclosure includes a use of a peptide, protein or polymer labelled with one or more substituted or unsubstituted 2,5-dithio-7-azabicyclo[2.2.1] heptane units in a medical application.

In another aspect, the present disclosure includes a use of a peptide, protein or polymer labelled with one or more substituted or unsubstituted 2,5-dithio-7-azabicyclo[2.2.1] heptane units in diagnosis of a diseases or condition.

In another aspect, the present disclosure includes a method of obtaining an antiviral and/or antimicrobial surface comprising treating a surface with substituted or unsubstituted 2,5-dihydroxy-1,4-dithiane.

In another aspect, the present disclosure includes an antiviral and/or antimicrobial surface obtained by a method of the present disclosure.

In another aspect, the present disclosure includes a surface treated with substituted or unsubstituted 2,5-dihydroxy-1,4-dithiane.

In another aspect, the present disclosure includes an antiviral and/or antimicrobial surface functionalized with one or more substituted or unsubstituted 2,5-dithio-7-azabicyclo[2.2.1]heptane units.

BRIEF DESCRIPTION OF THE DRAWINGS

In the following drawings, which represent by way of example only, various embodiments of the disclosure:

FIGS. 2A and 2B depict silica gel before (FIG. 2A) and after APES-dithiane modification (FIG. 2B).

FIG. 19A shows pipettes before addition of $I_2$. FIG. 19B shows pipettes just after addition of $I_2$. FIG. 19C shows elution with DCM, running through on the left, and forming a dark band on the right. FIG. 19D shows all of $I_2$ running through on the left, and no movement of the band on the right.

DETAILED DESCRIPTION

Figure 1:
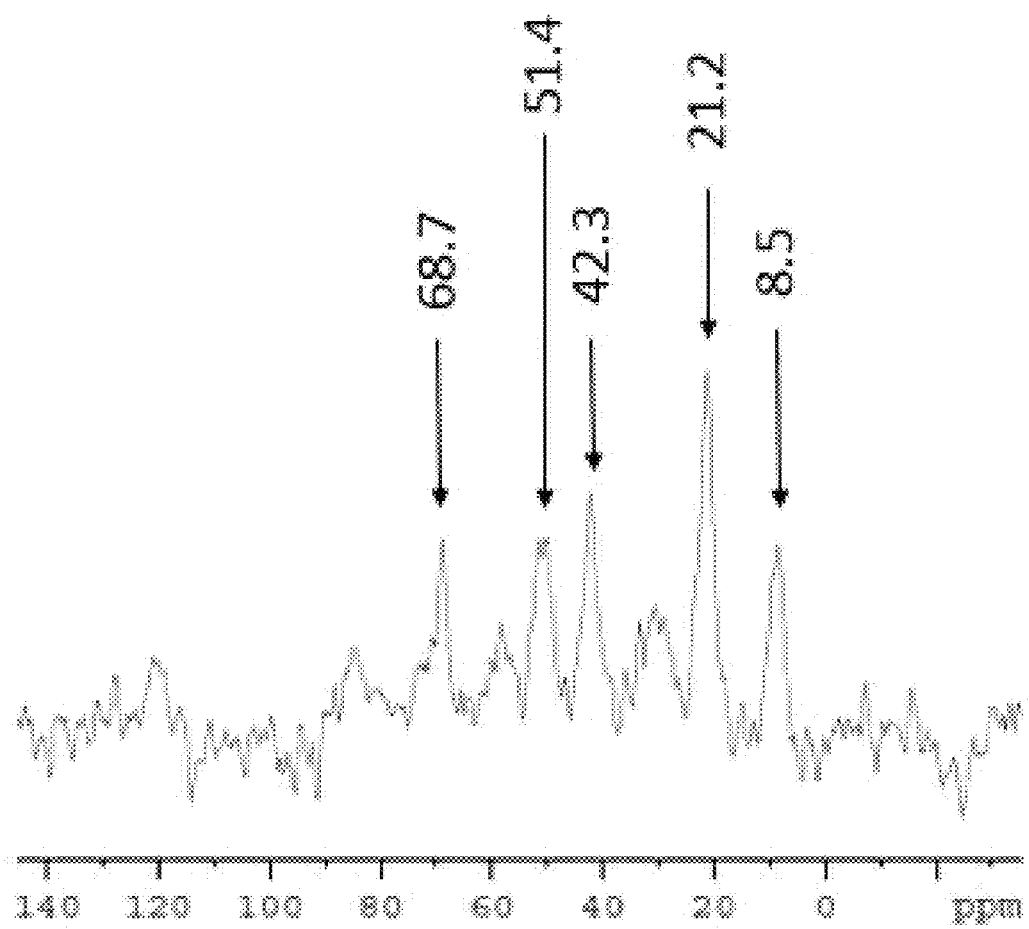
FIG. 1 depicts a solid state 13C nuclear magnetic resonance (NMR) spectra of aminopropyl-2,5-dithio-7-azabicyclo[2.2.1]heptane (APES-dithiane) modified silica gel, showing 5 peaks; 8.5, 21.2, 42.3 ppm for the aminopropyl portion and 51.4, 68.7 ppm for the bicyclic portion.

Various embodiments of the present disclosure are hereby provided in a non-limiting manner.

The term "redox active material" or "redox active materials" used herein refers to a material, a molecule, component of a molecule, a polymer, a substance or a surface that is capable of being oxidized or reduced. The redox active materials disclosed herein contain one or more 2,5-dithio-7-azabicyclo[2.2.1]heptane units acting as a reducing agent. These inherently electron rich materials are capable of reducing a variety of substances capable of accepting electrons (e.g. $I_2$, $Au^{3+}$, various quinones), becoming oxidized to cationic materials in the process. Additionally, treatment of these oxidized (cationic) materials with a suitable reducing agent such as for example sodium bisulfite can restore the redox active materials to their original reduced form.

As the 2,5-dithio-7-azabicyclo[2.2.1]heptane unit is chiral, the various compounds and formulas recited in the present application that involve substituted or unsubstituted 2,5-dithio-7-azabicyclo[2.2.1]heptane are intended to cover all epimers of such compounds and formulas. Even if a single epimer is represented in such compounds and formulas, all epimers are hereby covered and disclosed.

The person skilled in the art would understand that in some of the formulas of the present application, when only one enantiomer is shown, the intent is to cover both enantiomers as well as a mixture thereof i.e. a mixture of the illustrated enantiomer and its corresponding mirror image. In fact, for the sake of brevity, only one enantiomer is illustrated but it is indicated that both enantiomers are covered separately as well as a mixture of the two enantiomers. For example, such a mixture can be a racemic mixture.

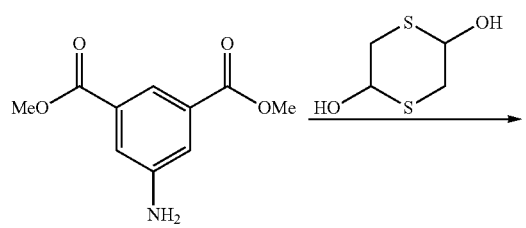

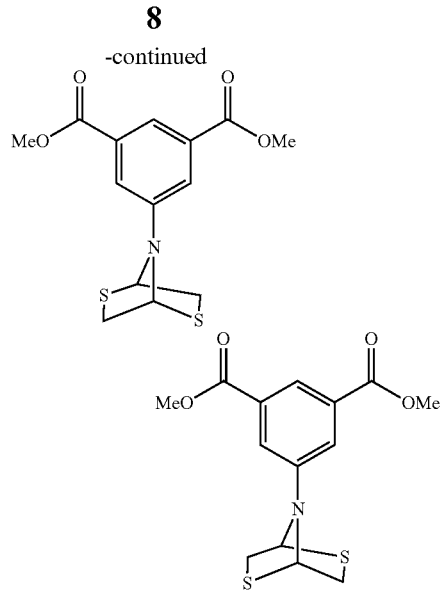

As it can be seen in the above scheme, the bicyclic dithiane is inherently chiral, by virtue of the position of the S atoms in the ring. The two products shown above are non-superimposable mirror images of each other. For example, when such bicyclic dithianes are made from amines, as shown above (i.e. in the absence of a chiral catalyst or chiral auxiliary) a racemic mixture (50:50 mixture of enantiomers) is obtained.

The term "alkyl" as used herein refers to a straight or branched alkyl. The alkyl can be unsubstituted or substituted with at least one substituent chosen from of a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "aryl" has used herein refers to a cyclic or polycyclic aromatic ring. The aryl can be, for example, unsubstituted or substituted with at least one substituent chosen from a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "heteroaryl" has used herein refers to an aromatic cyclic or fused polycyclic ring system having at least one heteroatom selected from the group consisting of N, O, and S. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on. These heteroaryl groups can be unsubstituted or substituted with at least one substituent chosen from a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "heterocyclyl" includes non-aromatic rings or ring systems that contain at least one ring having an at least one hetero atom (such as nitrogen, oxygen or sulfur). Preferably, this term includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, isothiazolidinyl, and imidazolidinyl. The heterocyclyl can be, for example, unsubstituted or substituted with at least one substituent chosen from the group consisting of a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "cycloalkyl" has used herein refers to a hydrocarbon ring which may contain or not double bonds. The cycloalkyl ring may be unsubstituted or substituted with at least one substituent chosen from a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

The term "aralkyl" has used herein refers to a refers to an alkyl or alkylenyl group substituted with at least one aryl group. The aralkyl may be unsubstituted or substituted with at least one substituent chosen from a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl, and $C_1$-$C_6$ hydroxyalkyl.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±10% of the modified term if this deviation would not negate the meaning of the word it modifies.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

In accordance with an aspect, there are provided redox active materials comprising at least one 2,5-dithio-7-azabicylo[2.2.1]heptane unit. The redox active materials may be synthesized through chemical modification of various solid phase carriers including for example cellulose, silica, chitosan, starch, cotton, paper, Celite™ polymers containing primary amino groups such as poly(ethyleneimine) and polyallylamine, (aminomethyl)polystyrene resin, TentaGel™-NH2 resins, diamino-trityl resins, and various peptides or proteins such as ubiquitin. These redox materials can also be produced by the polymerization of suitably functionalized monomers.

Accordingly, the inventors have determined that the 2,5-dithio-7-azabicyclo[2.2.1]heptane units are key functional groups that provide the presently disclosed redox active materials with unique redox properties and function. Accordingly, the disclosure provides in a first aspect redox materials comprising a solid phase carrier adorned with one or more 2,5-dithio-7-azabicyclo[2.2.1]heptane units.

In accordance with a first aspect, there is provided a redox active material of Formula I:

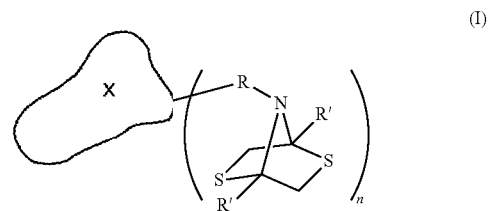

(I)

wherein X is a solid phase carrier; R is a linker or a chemical bond; n is any integer greater than 0; and R' is chosen from hydrogen, $C_1$-$C_{20}$ alkyl, $C_3$-$C_8$ cycloalkyl, $C_6$-$C_{12}$ aryl, $C_1$-$C_{12}$ heteroaryl, $C_1$-$C_{12}$ heterocyclyl and $C_6$-$C_{20}$ aralkyl, said alkyl, cycloalkyl, heteroaryl and heterocyclyl being unsubstituted or substituted with at least one substituent chosen from a halogen atom, —OH, —SH, —OMe, —SMe, —SPh, $C_1$-$C_6$ alkoxy, $C_1$-$C_8$ alkyl, $C_2$-$C_8$ alkenyl, $C_2$-$C_8$ alkynyl, $C_1$-$C_6$ aminoalkyl, $C_6$-$C_{20}$ aralkyl, $C_6$-$C_{12}$ aryl, $C_3$-$C_8$ cycloalkyl, $C_1$-$C_{12}$ heteroaryl, $C_1$-$C_{12}$ heterocyclyl and $C_1$-$C_6$ hydroxyalkyl, an enantiomer thereof, a mixture of said redox active material having Formula I and said enantiomer thereof, diastereoisomers thereof, stereoisomers thereof and epimers thereof.

For example, R' is independently an alkyl group, a phenyl group, and hydrogen. In one embodiment, R' is independently H. In another embodiment, R' is independently a methyl group.

For example, R' is methyl or ethyl. For example, R' is hydrogen. For example, R' is phenyl or benzyl.

For example, n is between 1 and $6 \times 10^{21}$ per gram of solid phase carrier. For example, n is between 1 and 10,000,000 per gram of solid phase carrier. For example, n is between 1 and 1,000,000 per gram of solid phase carrier.

In some embodiments, one or more nitrogen, carbon, sulfur, oxygen and/or hydrogen atoms of

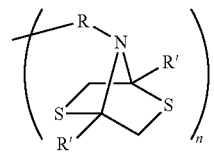

are each independently replaced with an isotope of the one or more nitrogen, carbon, sulfur, oxygen and/or hydrogen atoms.

In some embodiments, one or more hydrogen atoms of

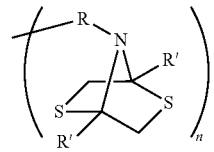

are each independently replaced with an isotope of hydrogen.

In some embodiments, one or more sulfur atoms of

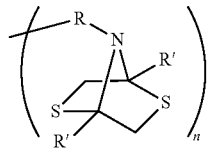

are each independently replaced with an isotope of sulfur.

In some embodiments, one or more nitrogen atoms of

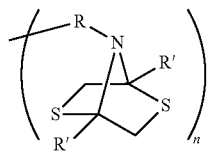

are each independently replaced with an isotope of nitrogen.

In some embodiments, one or more carbon atoms of

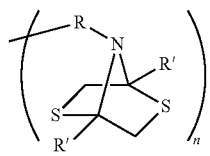

are each independently replaced with an isotope of carbon.

In accordance with another aspect, there is provided a redox active material comprising a solid phase carrier having at least one substituted or unsubstituted 2,5-dithio-7-azabicyclo[2.2.1]heptane unit connected to a surface thereof.

For example, the at least one 2,5-dithio-7-azabicyclo[2.2.1]heptane unit is connected to the surface of the solid phase carrier via a linker or a chemical bond.

For example, the solid phase carrier has between 1 and $6 \times 10^{21}$ 2,5-dithio-7-azabicyclo[2.2.1]heptane units connected to the surface thereof. For example, the solid phase carrier has between 1 and 10,000,000 2,5-dithio-7-azabicyclo[2.2.1]heptane units connected to the surface thereof. For example, the solid phase carrier has between 1 and 1,000,000 2,5-dithio-7-azabicyclo[2.2.1]heptane units connected to the surface thereof. For example, the solid phase carrier has about 0.25 to about 0.80 mmoles of 5-dithio-7-azabicyclo[2.2.1]heptane units connected to the surface thereof per gram of solid phase carrier.

For example, the linker R is chosen from aminopropyl triethoxysilane (APES), aminopropyl trimethoxy silane, 2-aminoethyl 3-aminopropyl trimethoxysilane (DAMS) and 3-2-(2-aminoethylamino) ethylaminopropyl-trimethoxysilane (TAMS).

For example, the linker terminates in a primary amine.
For example, without limitation, the linker is chosen from:

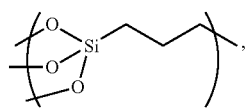

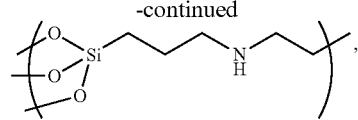

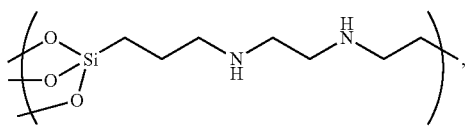

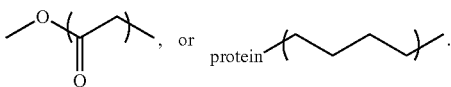

For example, the solid phase carrier is chosen from colloidal silica, silica, glass, glass wool, cellulose, pulp-derived cellulose, microcrystalline cellulose, nanocellulose, cotton, paper, chitin, chitosan, agarose, corn starch, potato starch, alumina, diatomaceous earth (Celite™), polysaccharide, peptide and protein such as peptide and protein containing lysine (e.g. ubiquitin), polymers, copolymers (e.g. amine functionalized polystyrenes, polyesters, polyamides), poly(ethyleneimine), polyallylamine, (aminomethyl)polystyrene, TentaGel™-NH2 resin, diaminoalkyl trityl resins, polyamides and polyesters from 5-aminoisophthalic acid, polyamides and polyesters from aminomalonic acid, and mixtures thereof. For example, the solid phase carrier can consist of polymeric material such as suitably functionalized polystyrene, poly(ethyleneimine), polyallylamine, a suitably functionalized polyester or a polyamide. The solid phase material may consist of a glass surface or paper derived from cellulose.

For example, the silica is chosen from colloidal silica, silica gel, silica glass, glass wool, silica composites, and mixtures thereof.

For example, the polysaccharide is chosen from cellulose, microcrystalline cellulose, microcellulose, nanocellulose, cotton, paper, starch (e.g. potato or corn starch), agarose, chitin, chitosan, polysaccharide composites, and mixtures thereof.

For example, the peptide or protein comprises at least one lysine residue.

For example, polymer is chosen from poly(ethyleneimine), polyallylamine, (aminomethyl)polystyrene, (2-aminoethyl)polystyrene, TentaGel™-NH2 resin, diamino trityl resin, amine-containing polyesters, amine-containing polyamides, copolymers and mixtures thereof, including copolymers of (aminomethyl)styrene and styrene.

For example, the material is in an oxidized form. For example, the material is in an reduced form.

In another aspect of the disclosure, the presently described redox active materials can undergo oxidation, with chlorine for example, where the 2,5-dithio-7-azabicyclo[2.2.1]heptane units gain a positive charge as shown in Scheme 1 below, and can now function as an anion exchange material. These cationic materials can subsequently be returned to their original, neutral state by reduction, with sodium bisulfite for example.

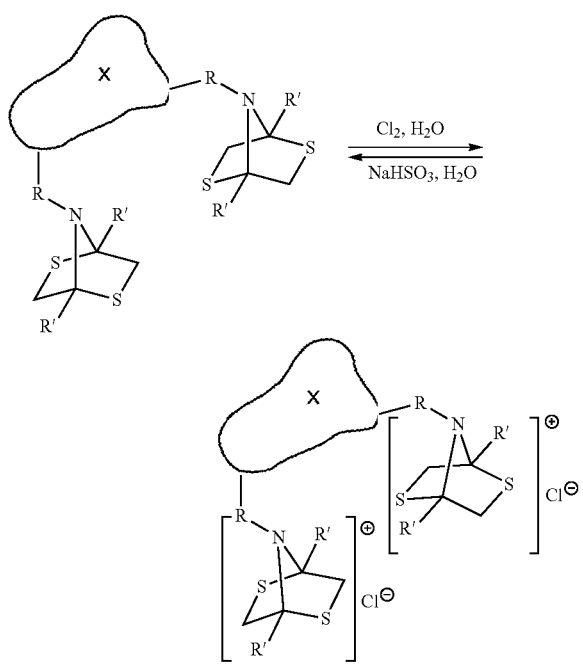

Scheme 1 depicts the generalized redox material undergoing oxidation with chlorine and becoming a cationic, anion exchange material. The oxidized form is capable of being reduced back to its original neutral form.

The presently disclosed redox active materials can be produced by a variety of processes.

Accordingly, an aspect relates to a process for preparing a redox active material, comprising
reacting a functionalized solid phase carrier having at least one primary amine bound at a surface thereof with a substituted or unsubstituted 2,5-dihydroxy-1,4-dithiane to obtain said redox active material.

Another aspect is a process for preparing a redox active material, comprising
functionalizing a solid phase carrier; and
reacting said functionalized solid phase carrier with a substituted or unsubstituted 2,5-dihydroxy-1,4-dithiane to obtain said redox active material.

For example, the solid phase carrier is functionalized by connecting at least one surface bound primary amine to the solid phase carrier.

For example, the functionalizing is carried out by incorporating a glycine, a lysine, an amine or polyamine trialkylsilane.

For example, the trialkylsilane is chosen from aminopropyl triethoxysilane (APES), aminopropyl trimethoxy silane, or 2-aminoethyl 3-aminopropyl trimethoxysilane (DAMS) and 3-2-(2-aminoethylamino) ethylaminopropyl-trimethoxysilane (TAMS).

For example, the functionalizing is carried out in the presence of water or toluene.

For example, the functionalizing is carried out at a temperature of about 10° C. to 140° C.

For example, the functionalizing is carried out for about 1 hour to 24 hours.

For example, the solid phase carrier is chosen from cellulose, microcellulose, nanocellulose, pulp-derived cellulose, paper, Celite™, starch (e.g. potato or corn starch), cotton, agarose, chitin, chitosan, polysaccharide composites, silica gel, silica glass, glass wool, silica composites, peptide and protein (e.g. ubiquitin), poly(ethyleneimine), polyallylamine, (aminomethyl)polystyrene, (2-aminoethyl)polystyrene, TentaGel™-NH2 resins, diamino trityl resins, amine functionalized polyesters, amine functionalized polyamides and mixtures thereof.

For example, the functionalized solid phase carrier is chosen from chitosan, 3-aminopropyl cotton, 3-aminopropyl cellulose, 3-aminopropyl silica, 3-aminopropyl modified glass wool, 3-aminopropyl starch, 3-aminopropyl cellulose pulp, 3-aminopropyl modified chitin, poly(ethyleneimine), polyallylamine, (aminomethyl)polystyrene, (2-aminoethyl)polystyrene, TentaGel™-NH2 resin, bis-(2-aminoethyl)-ether trityl resin, amine functionalized polyesters, amine functionalized polyamides, copolymers and mixtures thereof.

For example, a 2,5-dithio-7-azabicyclo[2.2.1]heptane-containing monomer can be used and the method can further comprises polymerizing a plurality of monomers to obtain a polymer.

Another aspect relates to a process for preparing a redox active material, comprising
reacting together a solid phase carrier, a primary amino linker and a substituted or unsubstituted 2,5-dihydroxy-1,4-dithiane to obtain said redox active material.

In another aspect, there is provided a process for preparing a redox active material, comprising
connecting to a surface of a solid phase carrier at least one substituted or unsubstituted 2,5-dithio-7-azabicyclo[2.2.1]heptane unit to obtain said redox active material.

For example, at least one 2,5-dithio-7-azabicyclo[2.2.1]heptane unit is connected to the solid phase carrier via a primary amino linker.

For example, the solid phase carrier comprises at least one surface bound hydroxyl group and said at least one 2,5-dithio-7-azabicyclo[2.2.1]heptane unit is connected to said solid phase carrier via said at least one surface bound hydroxyl group.

A further aspect herein disclosed relates to a process for preparing a redox active material, comprising
connecting to a surface of a solid phase carrier at least one substituted or unsubstituted 7-(prop-3-triethoxysilane)-(2,5-dithia-7-aza-bicyclo[2.2.1]heptane unit to obtain said redox active material.

For example, the solid phase carrier comprises at least one surface bound hydroxyl group and said at least one 7-(prop-3-triethoxysilane)-(2,5-dithia-7-aza-bicyclo[2.2.1]heptane unit is connected to said solid phase carrier via said at least one surface bound hydroxyl group.

For example, the solid phase carrier is chosen from cellulose, microcellulose, nanocellulose, pulp-derived cellulose, starch (e.g. potato or corn starch), agarose, chitin, polysaccharide composites, paper, Celite™, alumina, silica gel, silica glass, glass wool, cotton, silica composites, peptide and protein (e.g. ubiquitin), (aminomethyl)polystyrene, (2-aminoethyl)polystyrene, TentaGel™-NH2 resin, bis-(2-aminoethyl)-ether trityl resin, diaminoalkyl trityl resins, amine functionalized polyesters, amine functionalized polyamides and mixtures thereof.

For example, the primary amino linker is chosen from aminopropyl triethoxysilane (APES), aminopropyl trimethoxy silane, 2-aminoethyl 3-aminopropyl trimethoxysilane (DAMS) and 3-2-(2-aminoethylamino) ethylaminopropyl-trimethoxysilane (TAMS).

For example, the 2,5-dihydroxy-1,4-dithiane is substituted. For example, the 2,5-dihydroxy-1,4-dithiane is unsubstituted. For example, the 2,5-dihydroxy-1,4-dithiane is 2,5-dihydroxy-1,4-dithiane or 2,5-dimethyl-2,5-dihydroxy-1,4-dithiane.

For example, the reacting or connecting is carried out in the presence of a catalyst. For example, the catalyst chosen from magnesium acetate and sodium acetate.

For example, the reacting or connecting is carried out in the presence of a solvent. For example, the solvent is chosen from water, alcohol (e.g. ethanol), tetrahydrofuran (THF), dimethylformamide (DMF), and mixtures thereof.

For example, the reacting or connecting is carried out for about 1 hour to about 48 hours. For example, the reacting or connecting is carried out for about 1 hour to about 36 hours. For example, the reacting or connecting is carried out for about 2 hour to about 24 hours.

For example, the reacting or connecting is carried out at a temperature of about 10° C. to about 150° C. For example, the reacting or connecting is carried out at a temperature of about 10° C. to about 120° C. For example, the reacting or connecting is carried out at a temperature of about 20° C. to about 90° C.

For example, the obtained redox active material is isolated by filtration.

For example, the isolated redox active material is washed with water, optionally at least twice or at least three times.

For example, the washed redox active material is dried. For example, the drying is carried out in an oven at about 80° C. for about 24 hours. For example, the drying is carried out by washing with acetone and drying under reduced pressure.

Another aspect relates to a process for preparing a redox active material comprising polymerizing a 2,5-dithio-7-azabicyclo[2.2.1]heptane modified monomer by either anionic, cationic or radical polymerization to obtain said redox active material.

In a further aspect there is provided a process for preparing a redox active material comprising copolymerizing a 2,5-dithio-7-azabicyclo[2.2.1]heptane-containing monomer with a co-monomer in a ratio from 1:1 to 1:1000 (monomer: co-monomer), optionally in a ratio from 1:1 to 1:100, to obtain said redox active material.

For example, wherein the 2,5-dithio-7-azabicyclo[2.2.1]heptane-containing monomer is chosen from 7-(4-vinylphenyl)-2,5-dithia-7-azabicyclo[2.2.1]heptane (formula I), 7-(4-vinylbenzyl)-2,5-dithia-7-azabicyclo[2.2.1]heptane (formula II), 7-(4-vinylphenethyl)-2,5-dithia-7-azabicyclo[2.2.1]heptane (formula III), 7-(4-ethynylphenyl)-2,5-dithia-7-azabicyclo[2.2.1]heptane (formula IV), 7-(4-ethynylbenzyl)-2,5-dithia-7-azabicyclo[2.2.1]heptane (formula V), and 7-(4-ethynylphenethyl)-2,5-dithia-7-azabicyclo[2.2.1]heptane (formula VI):

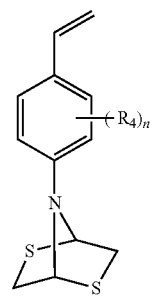

IA

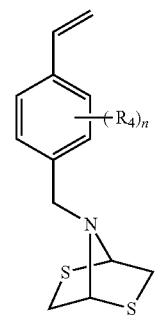

II

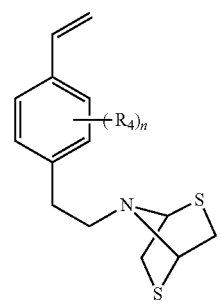

III

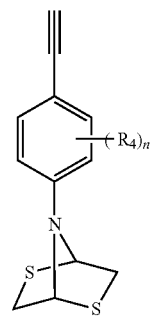

IV

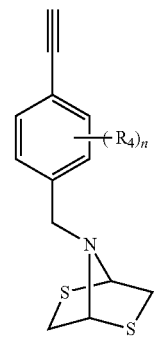

V

VI

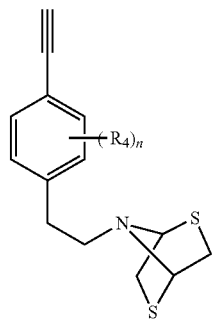

wherein R₄ is chosen from hydrogen, $C_1$-$C_{20}$ alkyl, $C_3$-$C_8$ cycloalkyl, $C_1$-$C_{12}$ heteroaryl, $C_1$-$C_{12}$ heterocyclyl and $C_6$-$C_{20}$ aralkyl and n is an integer from 1 to 4 such that the R₄ groups could be the same or different, attached to any position around the ring, an enantiomer thereof, a mixture of said redox active material having said formula and said enantiomer thereof, diastereoisomers thereof, stereoisomers thereof and epimers For example, the mixture is a racemic mixture.

For example, the co-monomer is chosen from styrene, 4-chloromethylstyrene, alkynylbenzene, 1-butene, vinylchloride, and acrylonitrile.

Another aspect relates to a process for preparing a redox active polyester comprising polymerizing or polycondensating a 2,5-dithio-7-azabicyclo[2.2.1]heptane-containing monomer with a linker agent diol (condensing agent) to obtain said redox active polyester material.

In a further aspect there is provided a process for preparing a redox active polyester material comprising copolymerizing or cocondensating a 2,5-dithio-7-azabicyclo[2.2.1] heptane-containing monomer with a co-monomer in a ratio from 1:1 to 1:1000 (monomer:co-monomer), optionally in a ratio from 1:1 to 1:100 to obtain said redox active polyester material.

For example, the 2,5-dithio-7-azabicyclo[2.2.1]heptane-containing monomer is chosen from 5-(2,5-dithia-7-azabicyclo[2.2.1]heptan-7-yl)isophthalic acid (formula VII), dimethyl 5-(2,5-dithia-7-azabicyclo[2.2.1]heptan-7-yl) isophthalate (formula VIII), 2-(2,5-dithia-7-azabicyclo [2.2.1]heptan-7-yl)terephthalic acid (formula IX), dimethyl 2-(2,5-dithia-7-azabicyclo[2.2.1]heptan-7-yl)terephthalate (formula X), 2-(2,5-dithia-7-azabicyclo[2.2.1]heptan-7-yl) malonic acid (formula XI), dimethyl 2-(2,5-dithia-7-azabicyclo[2.2.1]heptan-7-yl)malonate (formula XII), 2-(2,5-dithia-7-azabicyclo[2.2.1]heptan-7-yl)pentanedioic acid (XIII), dimethyl 2-(2,5-dithia-7-azabicyclo[2.2.1]heptan-7-yl)pentanedioate (XIV), 2-(2,5-dithia-7-azabicyclo[2.2.1] heptan-7-yl)hexanedioic acid (XV), and dimethyl 2-(2,5-dithia-7-azabicyclo[2.2.1]heptan-7-yl)hexanedioate (XVI):

VII

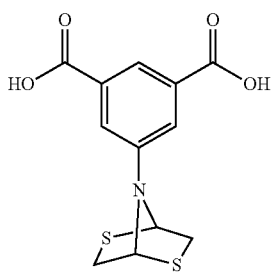

VIII

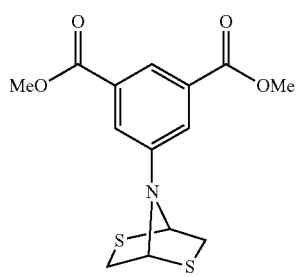

IX

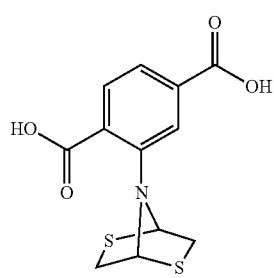

X

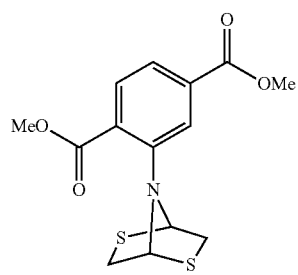

XI

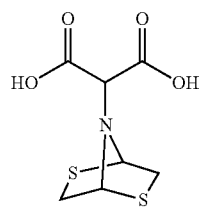

XII

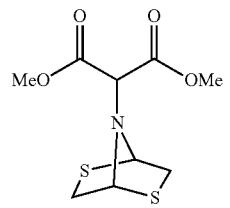

XIII

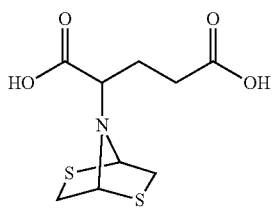

-continued

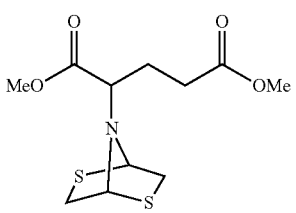
XIV

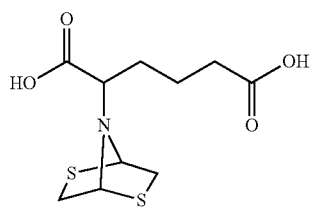
XV

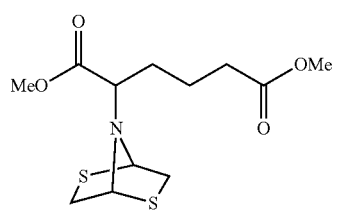
XVI an enantiomer thereof, a mixture of said redox active material having said formula and said enantiomer, diastereoisomers thereof, stereoisomers thereof and epimers thereof.

For example, the mixture is a racemic mixture.

For example, the linker diol is chosen from ethylene glycol, 1,3-propanediol, glycerol, 1,4-butanediol, 1,5-pentanediol, 1,6-hexanediol, resorcinol and 1,4-benzenediol.

For example, the co-monomer is chosen from isophthalic acid, terephthalic acid, dimethylisophthalate, diethylisophthalate, dimethylterephthalate, diethylterephthalate, dimethylmalonate, diethylmalonate, fumarate, dimethylfumarate, succinate, dimethylsuccinate, diethylsuccinate and mixtures thereof.

In another aspect there is provided herein a process for preparing a redox active polyamide material comprising polymerizing (or polycondensating) a 2,5-dithio-7-azabicyclo[2.2.1]heptane-containing monomer with a linker agent diamine (condensing agent) to obtain said redox active polyamide material.

Another aspect herein disclosed is a process for preparing a redox active polyamide material comprising copolymerizing (or cocondensating) a 2,5-dithio-7-azabicyclo[2.2.1]heptane-containing monomer with a co-monomer in a ratio from 1:1 to 1:1000 (monomer:co-monomer), optionally in a ratio from 1:1 to 1:100, to obtain said redox active polyamide material.

For example, 2,5-dithio-7-azabicyclo[2.2.1]heptane-containing monomer is chosen from 5-(2,5-dithia-7-azabicyclo[2.2.1]heptan-7-yl)isophthalic acid (formula VII), dimethyl 5-(2,5-dithia-7-azabicyclo[2.2.1]heptan-7-yl)isophthalate (formula VIII), 2-(2,5-dithia-7-azabicyclo[2.2.1]heptan-7-yl)terephthalic acid (formula IX), dimethyl 2-(2,5-dithia-7-azabicyclo[2.2.1]heptan-7-yl)terephthalate (formula X), 2-(2,5-dithia-7-azabicyclo[2.2.1]heptan-7-yl)malonic acid (formula XI), dimethyl 2-(2,5-dithia-7-azabicyclo[2.2.1]heptan-7-yl)malonate (formula XII), 2-(2,5-dithia-7-azabicyclo[2.2.1]heptan-7-yl)pentanedioic acid (XIII), dimethyl 2-(2,5-dithia-7-azabicyclo[2.2.1]heptan-7-yl)pentanedioate (XIV), 2-(2,5-dithia-7-azabicyclo[2.2.1]heptan-7-yl)hexanedioic acid (XV), and dimethyl 2-(2,5-dithia-7-azabicyclo[2.2.1]heptan-7-yl)hexanedioate (XVI):

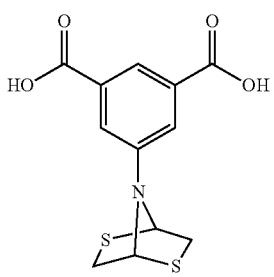
VII

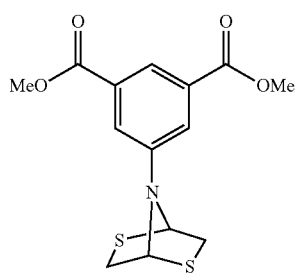
VIII

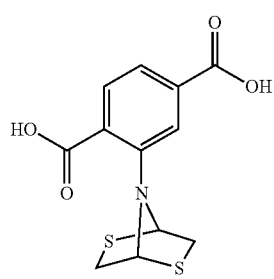
IX

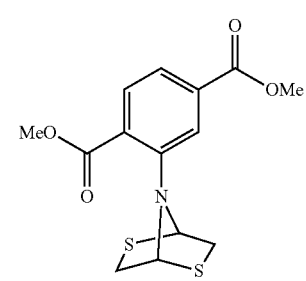
X

XI

XII 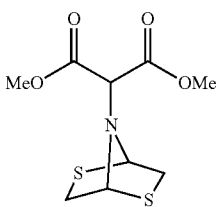

XIII 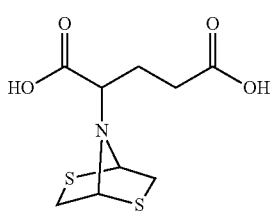

XIV 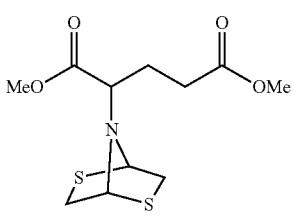

XV 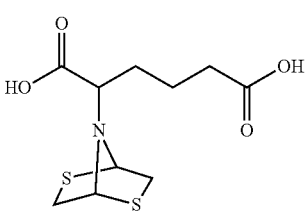

XVI 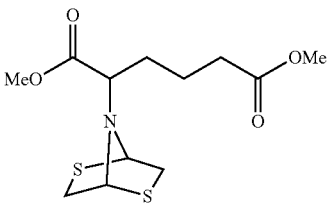

an enantiomer thereof, a mixture of said redox active material having said formula and said enantiomer, diastereoisomers thereof, stereoisomers thereof and epimers thereof.

For example, the 2,5-dithio-7-azabicyclo[2.2.1]heptane modified monomer is a mixture of stereoisomers in racemic form.

For example, the linker agent diamine is chosen from ethylenediamine, 1,3-propanediamine, 1,4-butanediamine, 1,5-pentanediamine, 1,6-hexanediamine, 1,3-benzenediamine, 1,4-benzenediamine, and mixtures thereof.

For example, the co-monomer is chosen from isophthalic acid, terephthalic acid, dimethylisophthalate, diethylisophthalate, dimethylterephthalate, diethylterephthalate, dimethylmalonate, diethylmalonate, fumarate, dimethylfumarate, succinate, dimethylsuccinate, diethylsuccinate and mixtures thereof.

In one embodiment, the redox active materials are produced, as described in Scheme 2 below, from a solid phase carrier that contains surface-bound primary amines, either inherent in the solid phase carrier or chemically attached to the solid phase carrier by incorporation of glycine, a lysine, a similar amino acid, or an amine or polyamine functionalized trialkylsilane such as aminopropyl triethoxysilane, aminopropyl trimethoxy silane, or 2-aminoethyl 3-aminopropyl trimethoxysilane (DAMS) or 3-2-(2-aminoethylamino) ethylaminopropyl-trimethoxysilane (TAMS). These solid phase carriers containing surface-bound primary amines are then reacted with 2,5-dihydroxy-1,4-dithiane or 2,5-dimethyl-2,5-dihydroxy-1,4-dithiane, in a suitable solvent such as water, water-alcohol mixture or water-tetrahydrofuran (THF) or water-dimethylformamide (DMF) mixture, with a catalyst such as magnesium acetate or sodium acetate. Reaction times are between 1 and 24 hours, at temperatures between 20° C. and 90° C. Both epimers of the 2,5-dithio-7-azabicyclo[2.2.1]heptane unit (the 2,5-dithio-7-azabicyclo[2.2.1]heptane unit is chiral) are produced upon functionalization.

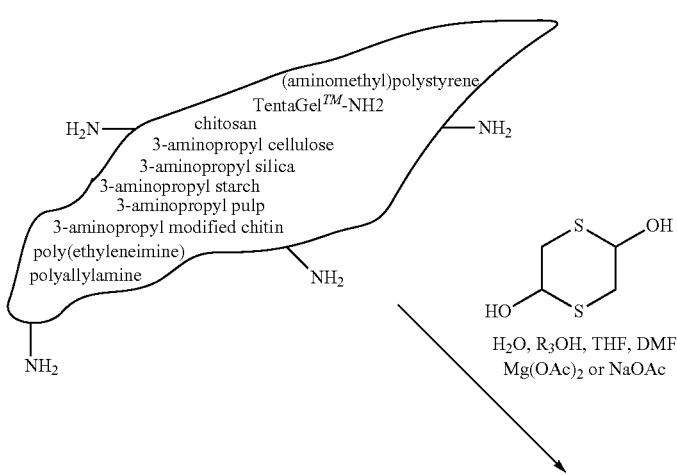

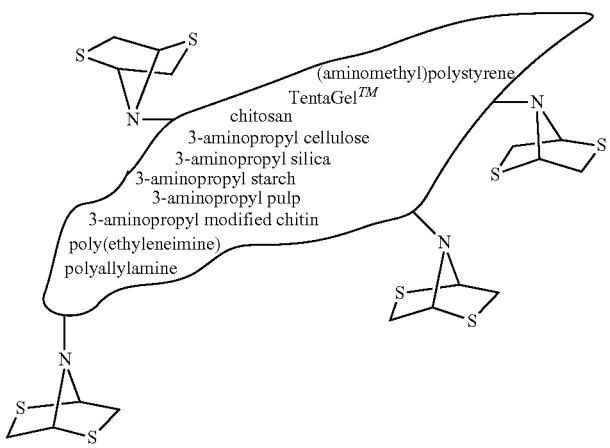

Scheme 2 depicts a general reaction scheme for the chemical modification of materials or polymers containing primary amines to form 2,5-dithio-7-azabicyclo[2.2.1]heptane units. This is accomplished in water or a mixed water-alcohol ($R_3OH$) as solvent using 2,5-dihydroxy-1,4-dithiane and a suitable catalyst. $R_3$ can be chosen from C1-C6 alkyls.

In another aspect (as described in Scheme 3), the presently disclosed redox active materials can also be obtained via a one-pot procedure by stirring a solid phase carrier that does not contain primary amines, with a primary amine linker molecule; 2,5-dihydroxy-1,4-dithiane or 2,5-dimethyl-2,5-dihydroxy-1,4-dithiane; a suitable catalyst such as magnesium acetate or sodium acetate, in a suitable solvent such as water, alcohol-water mixtures or THF-water mixtures, at temperatures ranging from 20° C.-100° C., and times ranging from 2 hours to 24 hours. Both epimers of the 2,5-dithio-7-azabicyclo[2.2.1]heptane unit are produced upon functionalization.

The primary amine linker molecule can for example be aminopropyl triethoxysilane (APES), aminopropyl trimethoxy silane, or 2-aminoethyl 3-aminopropyl trimethoxysilane (DAMS) or 3-2-(2-aminoethylamino) ethylaminopropyl-trimethoxysilane (TAMS),

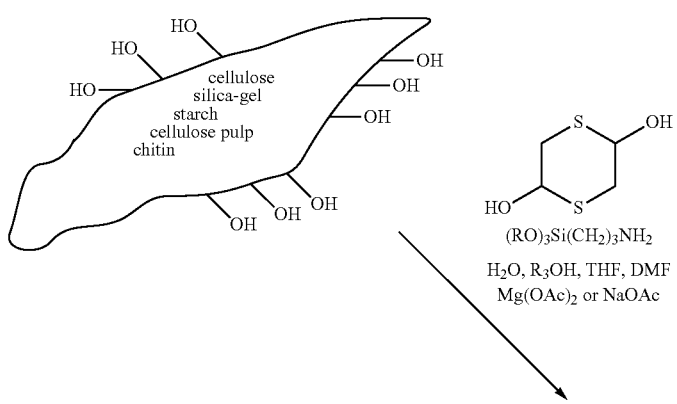

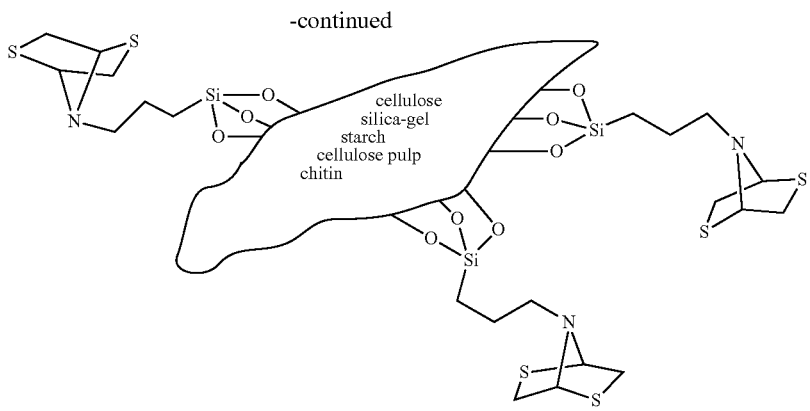

Scheme 3 depicts a general reaction scheme for functionalizing solid phase carrier materials containing surface-bound hydroxyl groups such as for example cellulose, cellulose pulp, paper, starch, cotton, colloidal silica, silica gel, glass wool, chitin, Celite™ potato starch, corn starch. The functionalization occurs in a one-pot reaction by stirring and heating slightly, for example at temperatures ranging from 20° C.-100° C., a mixture of solid phase carrier; a primary amine linker molecule such as aminopropyl triethoxysilane (APES); 2,5-dihydroxy-1,4-dithiane; a suitable catalyst such as magnesium acetate or sodium acetate, in a suitable solvent.

In another aspect of this disclosure, the presently disclosed redox active materials can be synthesized by polymerization of a suitable monomer (Scheme 4) functionalized with the 2,5-dithio-7-azabicyclo[2.2.1]heptane, that is then polymerized in a normal polymerization or copolymerization process. Detailed examples are described in Example 10.

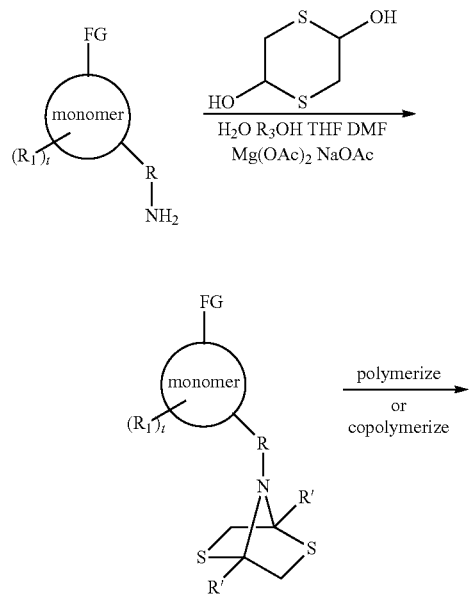

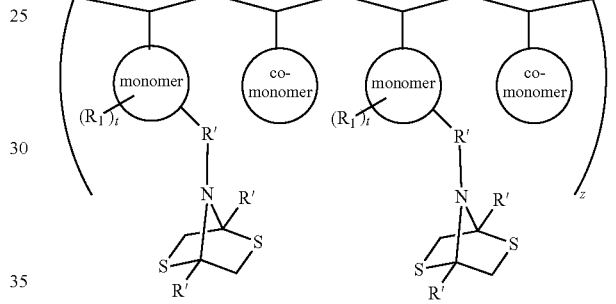

Scheme 4 depicts a general scheme for conversion of an amine functionalized styrene-based monomer into a 2,5-dithio-7-azabicyclo[2.2.1]heptane unit, and its subsequent polymerization or co-polymerization by standard methods. In this scheme, FG is a polymerizable functional group such as vinyl or ethynyl, $R_1$ is chosen from hydrogen, $C_1$-$C_{20}$ alkyl, $C_3$-$C_8$ cycloalkyl, $C_1$-$C_{12}$ heteroaryl, $C_1$-$C_{12}$ heterocyclyl and $C_6$-$C_{20}$ aralkyl and t is an integer from 1 to 4 such that the $R_1$ groups (if more than one) could be the same or different, attached to any position around the ring. Moreover, z is an integer from 10 to 200, R, R' and $R_3$ are as previously defined. Co-monomers include styrene, substituted styrenes, 1-butene, vinyl chloride, and acrylonitrile. The ratio of monomer to co-monomer can range from 1:1 to 1:100 to 1:1000. The distribution of monomer and co-monomer in the copolymer can vary from alternating units (A-B-A-B-A-B) to a random distribution (A-A-B-A-B-B-B-A-B-A-A-), where A is the functionalized unit and B is unfunctionalized.

In another aspect of this disclosure the presently disclosed redox active materials can be synthesized by the polymerization (polycondensation) or co-polymerization of 2,5-dithio-7-azabicyclo[2.2.1]heptane-containing monomers capable of forming polyesters. The bicyclic dithiane-containing monomer can be polymerized into a redox active polyester by reaction with, for example 1,3-propane diol.

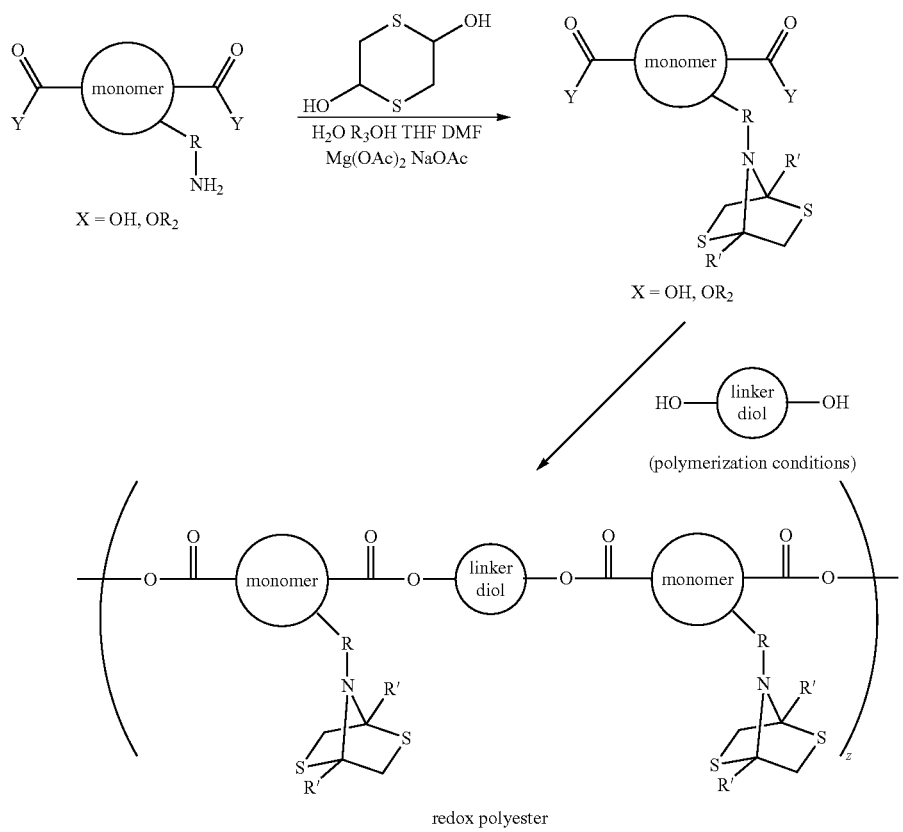

Scheme 5a depicts a general scheme for the synthesis of redox active polyesters from 2,5-dithio-7-azabicyclo[2.2.1]heptane-containing monomers. The bi-functional monomers include the amine functionalized phthalate system, isophthalate, terephthalate, 2-amino malonate, aspartate and glutamate. The linker diol (the condensing agent) are diols that include ethylene glycol, 1,3-propanediol, 1,4-butanediol, glycerol, resorcinol. Y is chosen from methoxy, ethoxy, 2,2,2-trichloroethoxy, benzyloxy. Co-polymerization with co-monomers is possible using the phthalate systems, malonates, fumarates and succinates. The ratio of monomer to co-monomer can vary from 1:1 to 1:100. Copolymerization results in dilution of the 2,5-dithio-7-azabicyclo[2.2.1]heptane unit in the material.

In another aspect of this disclosure the presently disclosed redox active materials can be synthesized by the polymerization (polycondensation) or co-polymerization of 2,5-dithio-7-azabicyclo[2.2.1]heptane-containing monomers capable of forming polyamides. The bicyclic dithiane-containing monomer can be polymerized into a redox active polyamide by reaction with 1,4-butane diamine for example.

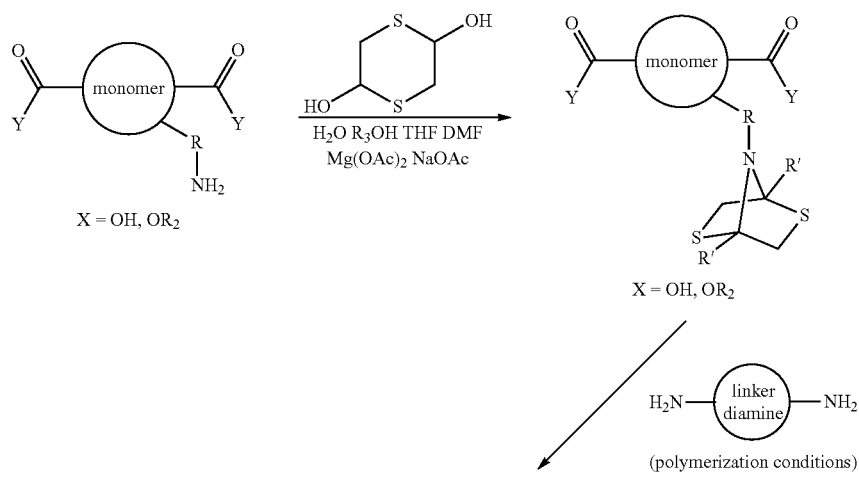

-continued

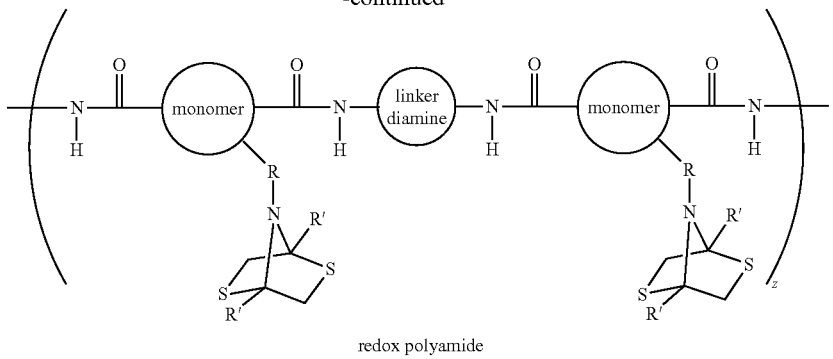

redox polyamide

Scheme 5b depicts a general scheme for the synthesis of redox active polyamides from 2,5-dithio-7-azabicyclo[2.2.1]heptane-containing monomers. The bi-functional monomers include the amine functionalized phthalate system, isophthalate, terephthalate, 2-amino malonate, aspartate and glutamate. Linker diamines include ethylenediamine, 1,3-propanediamine, 1,4-butanediamine, 1,6-hexanediamine, 1,4-diaminobenzene, 1,3-diaminobenzene, any 1,n-alkyldiamine, tris(2-aminoethyl)amine or tris(3-aminopropyl)amine. Y is chosen from methoxy, ethoxy, 2,2,2-trichloroethoxy, benzyloxy. Co-polymerization with co-monomers is possible using the phthalate systems, malonates, fumarates and succinates. The ratio of monomer to co-monomer can vary from 1:1 to 1:100. Copolymerization results in dilution of the 2,5-dithio-7-azabicyclo[2.2.1]heptane unit in the material.

The presently disclosed neutral 2,5-dithio-7-azabicyclo[2.2.1]heptane functionalized solid materials behave as reducing reagents. These redox active materials have the ability to reduce metals such as precious metals in their oxidized oxidation state, and bind the zero oxidation state metals, often as a nanoparticle. As shown in Scheme 5, the materials may be used to reduce AuCl$_3$ to Au$^0$. Additionally, these materials can be oxidized with mild oxidizing agents such a chlorine gas to form the cationic version of the 2,5-dithio-7-azabicyclo[2.2.1]heptane unit. These oxidized materials can act as anion exchange resins.

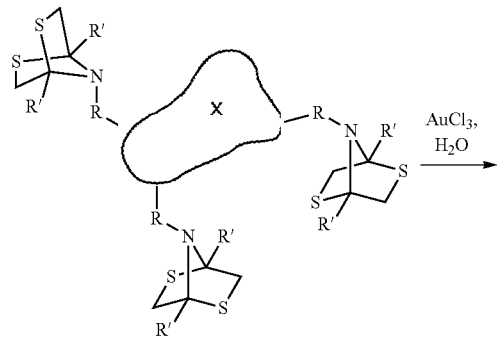

-continued

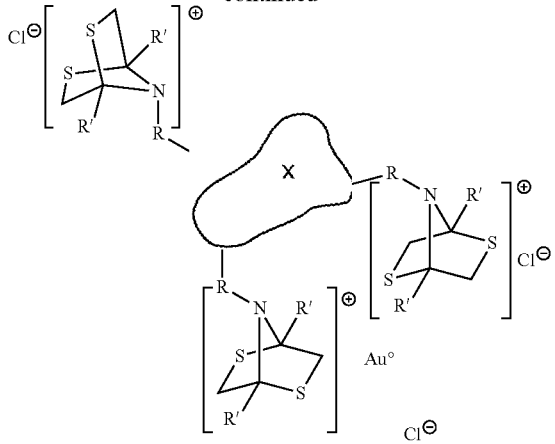

Scheme 6 illustrates the general reduction chemistry that the presently disclosed redox active materials undergo with metals of low reduction potential, such as gold 3+.

Also provided in an aspect is a redox active material obtained according to a process herein disclosed.

Accordingly, there is provided in another aspect a method for recovering a metal, comprising:
  reacting a metal in oxidized state with the redox active material herein disclosed or the redox active material obtained according to the process herein disclosed so as to reduce the metal; and
  obtaining a reduced metal that is adsorbed to the redox active material.

For example, the metal in oxidized state is present in an aqueous solution.

For example, the process further comprises isolating the reduced metal, optionally by burning off the redox active material.

For example, the process further comprises recovering said reduced metal by filtration.

For example, the metal is chosen from Au, Pt, Cu, Hg and Ag.

For example, the metal is AuCl$_3$, Au(CN)$_3$, Au$_2$(S2O3)$_3$, Au(S2O3)$_n$$^{m-}$ and said reduced metal is Au$^0$.

For example, the metal in oxidized state is copper sulfate and the reduced precious metal is Cu$^0$.

For example, the reduced metal is in nanoparticle form.

For example, the metal is reacted with said redox active material for about 10 minutes to about 6 hours. For example, the metal is reacted with said redox active material for about 10 minutes to about 5 hours. For example, the metal is reacted with said redox active material for about 10 minutes to about 4 hours. For example, the metal is reacted with said redox active material for about 10 minutes to about 3 hours. For example, the metal is reacted with said redox active material for about 10 minutes to about 2 hours. For example, the metal is reacted with said redox active material for about 10 minutes to about 1 hour.

For example, the metal is reacted with said redox active material at a pH of about 1 to about 12. For example, the metal is reacted with said redox active material at a pH of about 1 to about 5. The metal is reacted with said redox active material at a pH of about 9 to about 12. The metal is reacted with said redox active material at a pH of about 5 to 9.

In yet another aspect, there is provided a use of the redox active material disclosed herein or of the redox active material obtained according to the process disclosed herein as an anion exchange material, a halogen scavenger agent, a water filtration agent, a halogen filter agent, an air, water and/or petroleum detector agent, in dialysis or in drug synthesis.

For example, the redox active material is in an oxidized form and is used as an anion exchange material.

For example, the redox active material is in an oxidized form and is used as an anion exchange material for the removal of phosphate.

For example, the redox active material is used as a water filter agent for removing contaminants optionally chosen from copper and mercury.

The present disclosure also relates to various compounds.

In an aspect, there is provided a compound of formula:

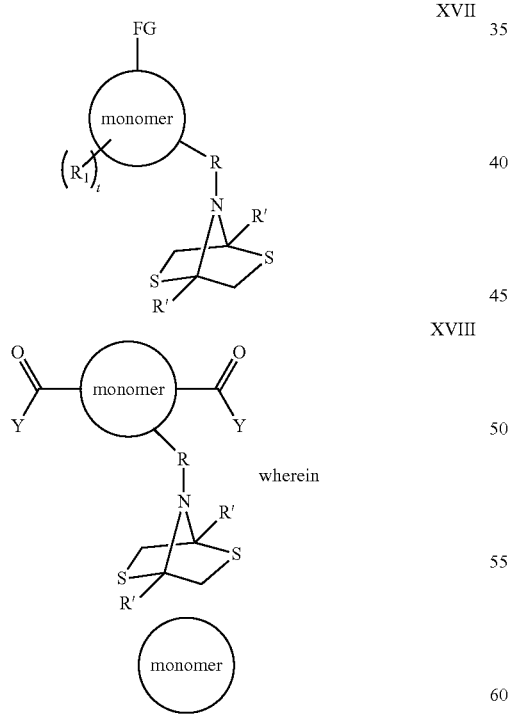

XVII

XVIII wherein is chosen from $C_1$-$C_{20}$ alkyl, $C_3$-$C_8$ cycloalkyl, $C_6$-$C_{12}$ aryl, $C_1$-$C_{12}$ heteroaryl, $C_1$-$C_{12}$ heterocyclyl and $C_6$-$C_{20}$ aralkyl, and wherein R, R', are as previously defined; $R_1$ is chosen from hydrogen, $C_1$-$C_{20}$ alkyl, $C_3$-$C_8$ cycloalkyl, $C_1$-$C_{12}$ heteroaryl, $C_1$-$C_{12}$ heterocyclyl and $C_6$-$C_{20}$ aralkyl, and t is an integer from 1 to 4 such that the $R_1$ groups (if more than one) could be the same or different, attached to any position around the ring; FG is a polymerizable functional group such as vinyl or ethynyl, and Y is hydroxy, methoxy, ethoxy, 2,2,2-trichloroethoxy or benzyloxy, an enantiomer thereof, a mixture of compound having said formula and said enantiomer, diastereoisomers thereof, stereoisomers thereof and epimers thereof.

Another aspect relates to a compound of any one of formulas I to XVI.

For example, the compound is chosen from:

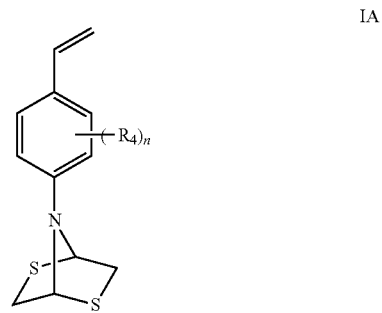

IA

II

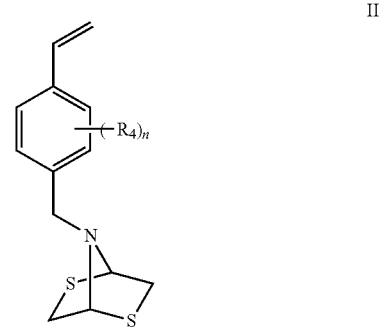

III

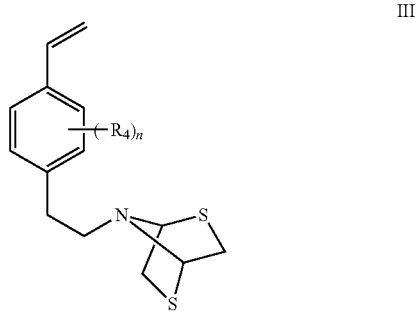

IV

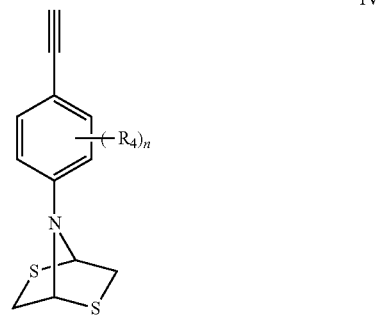

V
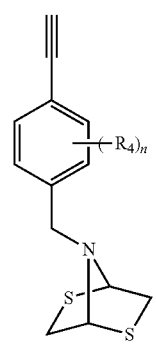
VI
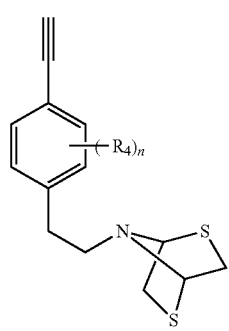
VII
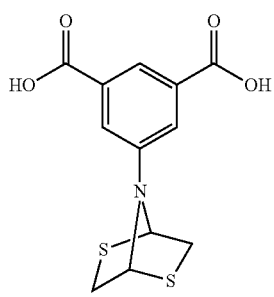
VIII
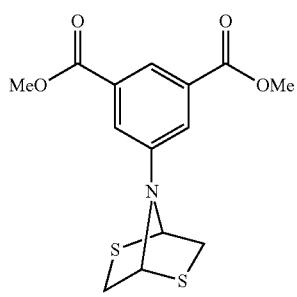
IX
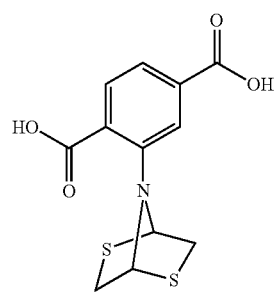
X
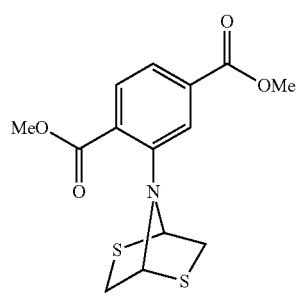
XI
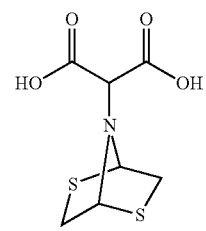
XII
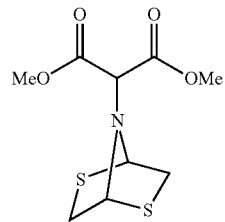
XIII
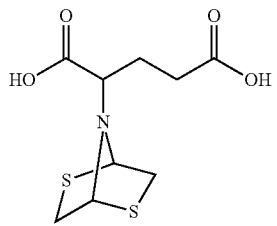
XIV
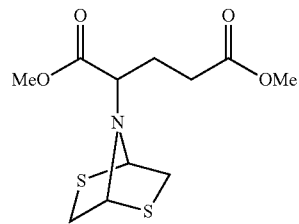
XV
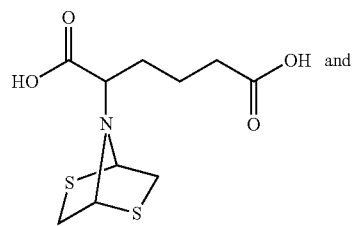
and -continued

XVI

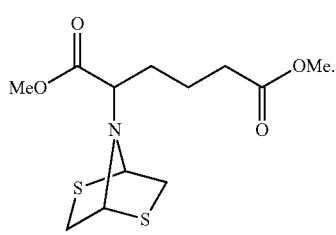

wherein R$_4$ is as previously defined,
an enantiomer thereof, a mixture of compound having said formula and said enantiomer, diastereoisomers thereof, stereoisomers thereof and epimers thereof.

In some embodiments, one or more nitrogen, carbon, sulfur, oxygen and/or hydrogen atoms of the 5-dithio-7-azabicyclo[2.2.1]heptane unit as described herein are each independently replaced with an isotope of the one or more nitrogen, carbon, sulfur, oxygen and/or hydrogen atoms.

In some embodiments, one or more hydrogen atoms of the 5-dithio-7-azabicyclo[2.2.1]heptane unit as described herein are each independently replaced with an isotope of hydrogen.

In some embodiments, one or more sulfur atoms of the 5-dithio-7-azabicyclo[2.2.1]heptane unit as described herein are each independently replaced with an isotope of sulfur.

In some embodiments, one or more nitrogen atoms of the 5-dithio-7-azabicyclo[2.2.1]heptane unit as described herein are each independently replaced with an isotope of nitrogen.

In some embodiments, one or more carbon atoms of the 5-dithio-7-azabicyclo[2.2.1]heptane unit as described herein are each independently replaced with an isotope of carbon.

In some embodiments, one or more nitrogen, carbon, sulfur, oxygen and/or hydrogen atoms of the substituted or unsubstituted 2,5-dihydroxy-1,4-dithiane as described herein are each independently replaced with an isotope of the one or more nitrogen, carbon, sulfur, oxygen and/or hydrogen atoms.

In some embodiments, one or more hydrogen atoms of the substituted or unsubstituted 2,5-dihydroxy-1,4-dithiane as described herein are each independently replaced with an isotope of hydrogen.

In some embodiments, one or more sulfur atoms of the substituted or unsubstituted 2,5-dihydroxy-1,4-dithiane as described herein are each independently replaced with an isotope of sulfur.

In some embodiments, one or more nitrogen atoms of the substituted or unsubstituted 2,5-dihydroxy-1,4-dithiane as described herein are each independently replaced with an isotope of nitrogen.

In some embodiments, one or more carbon atoms of the substituted or unsubstituted 2,5-dihydroxy-1,4-dithiane as described herein are each independently replaced with an isotope of carbon.

In some embodiments, one or more nitrogen, carbon, sulfur, oxygen and/or hydrogen atoms of the 2,5-dithio-7-azabicyclo[2.2.1]heptane-containing monomer as described herein are each independently replaced with an isotope of the one or more nitrogen, carbon, sulfur, oxygen and/or hydrogen atoms.

In some embodiments, one or more hydrogen atoms of the 2,5-dithio-7-azabicyclo[2.2.1]heptane-containing monomer as described herein are each independently replaced with an isotope of hydrogen.

In some embodiments, one or more sulfur atoms of the 2,5-dithio-7-azabicyclo[2.2.1]heptane-containing monomer as described herein are each independently replaced with an isotope of sulfur.

In some embodiments, one or more nitrogen atoms of the 2,5-dithio-7-azabicyclo[2.2.1]heptane-containing monomer as described herein are each independently replaced with an isotope of nitrogen.

In some embodiments, one or more carbon atoms of the 2,5-dithio-7-azabicyclo[2.2.1]heptane-containing monomer as described herein are each independently replaced with an isotope of carbon.

In some embodiments, the isotope of hydrogen is chosen from deuterium and tritium.

In some embodiments, the isotope of sulfur is chosen from $^{33}$S, $^{34}$S, $^{35}$S, and $^{36}$S.

In some embodiments, the isotope of nitrogen is chosen from $^{13}$N and $^{15}$N.

In some embodiments, the isotope of carbon is chosen from $^{11}$C, $^{13}$C, and $^{14}$C.

In another aspect, the present disclosure includes a redox-active material of the present disclosure or a redox-active material obtained from a process of the present disclosure for use in a medical application.

In another aspect, the present disclosure includes a redox-active material of the present disclosure or a redox-active material obtained from a process of the present disclosure for use in diagnosis of a disease or condition.

In another aspect, the present disclosure includes a use of a redox-active material of the present disclosure or a redox-active material obtained from a process of the present disclosure in a medical application.

In another aspect, the present disclosure includes a use of a redox-active material of the present disclosure or a redox-active material obtained from a process of the present disclosure in diagnosis of a disease or condition.

In another aspect, the present disclosure includes a peptide, protein or polymer labelled with one or more substituted or unsubstituted 2,5-dithio-7-azabicyclo[2.2.1]heptane units for use in a medical application.

In another aspect, the present disclosure includes a peptide, protein or polymer labelled with one or more substituted or unsubstituted 2,5-dithio-7-azabicyclo[2.2.1]heptane units for use in diagnosis of a disease or condition.

In another aspect, the present disclosure includes a use of a peptide, protein or polymer labelled with one or more substituted or unsubstituted 2,5-dithio-7-azabicyclo[2.2.1] heptane units in a medical application.

In another aspect, the present disclosure includes a use of a peptide, protein or polymer labelled with one or more substituted or unsubstituted 2,5-dithio-7-azabicyclo[2.2.1] heptane units in diagnosis of a diseases or condition.

In another aspect, the present disclosure includes a method of obtaining an antiviral and/or antimicrobial surface comprising treating a surface with substituted or unsubstituted 2,5-dihydroxy-1,4-dithiane.

In another aspect, the present disclosure includes an antiviral and/or antimicrobial surface obtained by a method of the present disclosure.

In another aspect, the present disclosure includes a surface treated with substituted or unsubstituted 2,5-dihydroxy-1,4-dithiane.

In another aspect, the present disclosure includes an antiviral and/or antimicrobial surface functionalized with one or more substituted or unsubstituted 2,5-dithio-7-azabicyclo[2.2.1]heptane units.

In some embodiments, the medical application can be antimicrobial suture, liquid filtration, optionally water or blood filtration, air filtration, dialysis, and removal of metals. For example, the removal of metals can be removal of heavy metals.

In some embodiments, the diagnosis of the disease or condition is through mass spectrometry of a biomarker associated with the disease or condition that is functionalized with at least one of the redox-active material of the present disclosure. For example, the biomarker is functionalized with one or more substituted or unsubstituted 2,5-dithio-7-azabicyclo[2.2.1]heptane units of the disclosure. For example, the biomarker is functionalized with one or more 2,5-dihydroxy-1,4-dithianes.

In some embodiments, the diagnosis of the disease or condition is through mass spectrometry of the peptide, protein or polymer of the present disclosure, and the peptide, protein or polymer of the present disclosure is a biomarker associated with the disease or condition.

In some embodiments, the surface with substituted or unsubstituted 2,5-dihydroxy-1,4-dithiane units of the present disclosure is chosen from a phone screen, colloidal silica, silica composites, laminates, counter-tops, textiles and cloths, air and/or water filtration materials, door handle, surface coatings, keyboards, faucets, and shopping carts. For example, the textiles and cloths are chosen from clothing, bed sheets, curtains and masks.

In some embodiments, the antiviral and/or antimicrobial surface is chosen from a phone screen, colloidal silica, silica composites, laminates, counter-tops, textiles and cloths, air and/or water filtration materials, door handle, surface coatings, keyboards, faucets, and shopping carts. For example, the textiles and cloths are chosen from clothing, bed sheets, curtains and masks.

EXAMPLES

The redox active materials can be synthesized from a variety of substrates in a variety of ways.

Example 1—Modified Silica Gel

Silica gel 60 (10 g) is reacted with (3-aminopropyl)triethyoxysilane (APES) (1.5 g) in boiling water (50 mL) for 2 hours After being allowed to cool to 30° C., an aqueous suspension of 2,5-dihydroxy-1,4-dithiane (1 g) in 20 mL of water, which had been previously stirred with either Mg(OAc)$_2$ or NaOAc for 20 minutes at 30° C., is added. This combined aqueous suspension is stirred between 30° C. and 60° C. for 24 hours. The modified silica gel is isolated by filtration, and washed with 50° C. water three times. The material can be used damp in aqueous applications. The material can be dried by placing in an oven at 80° C. for 24 hours. It can also be dried in the filter funnel by washing with acetone two times, placed in a round bottom flask, and dried under reduced pressure.

Example 2—Modified Silica Gel

Silica gel 60 (10 g) is reacted with APES (1.5 g) in boiling toluene (50 mL) for 6 hours. After cooling to 30° C., the material is isolated by filtration. The dried or partially dried material is added to an aqueous suspension of 2,5-dihydroxy-1,4-dithiane (1 g) in 50 mL of water, which had been previously stirred with either Mg(OAc)$_2$ or NaOAc for 20 minutes at 30° C. This combined aqueous suspension is stirred between 30° C. and 60° C. for 24 hours. The modified silica gel is isolated by filtration, and washed with 50° C. water three times. The material can be used wet. The material can be dried by placing in an oven at 80° C. for 24 hours. It can also be dried in the filter funnel by washing with acetone two times, placed in a round bottom flask, which is subsequently placed on the rotovap and dried.

Example 3—Modified Silica Gel

Silica gel 60 (10 g), APES (1.5 g), and 2,5-dihydroxy-1,4-dithiane (1.0 g) and Mg(OAc)$_2$ (0.25 g) are stirred together in a 250 mL round bottom flask containing 75 mL of water, and stirred for 24 hours between 30° C. and 60° C. Modified silica gel is isolated by filtration and used wet, or dried with acetone as described above.

Example 4—Modified Silica Gel

Silica gel 60 (10 g) is stirred in toluene (50 mL) and 7-(prop-3-triethoxysilane)-(2,5-dithia-7-aza-bicyclo[2.2.1]heptane (2 g) is added to this slurry. The reaction is heated to reflux (condenser attached) from for 6 hours. The cooled reaction is filtered, the modified silica gel is washed (×2) with acetone (with filtering). Evaporation of the filtrate results in recovery of 0.5 g of unreacted 7-(prop-3-triethoxysilane)-(2,5-dithia-7-aza-bicyclo[2.2.1]heptane. The material is ready for use, but can be dried further under vacuum in a suitable round bottom flask (RBF). This reaction can be done using water as solvent also.

Modified silica-gel based materials made via Examples 1-4 are indistinguishable. All materials have the distinguishing chemical reducing properties when tested using $I_2$ in dry column chromatography (DCC) as described in FIG. 8, and $AuCl_3$ in water as qualitative tests.

Example 5—Modified Microcrystalline Cellulose

Microcrystalline cellulose (10 g) is reacted with APES (2 g) in boiling water (50 mL) for 2 hours. After being cooled to 30° C., an aqueous suspension of 2,5-dihydroxy-1,4-dithiane (1 g) in 20 mL of water, which had been previously stirred with either Mg(OAc)$_2$ or NaOAc for 20 minutes at 30° C., is added. This combined aqueous suspension is stirred between 30° C. and 60° C. for 24 hours. The modified microcrystalline cellulose is isolated by filtration, and washed with 50° C. water three times. The material can be used wet. The material can be dried by placing in an oven at 80° C. for 24 hours. It can also be dried in the filter funnel by washing with acetone two times, placed in a round bottom flask, which is subsequently dried under reduced pressure.

Example 6—Modified Microcrystalline Cellulose

Microcrystalline cellulose (10 g) is reacted with APES (2 g) in boiling toluene (50 mL) for 6 hours. After cooling to 30° C., the material is isolated by filtration. The dried or partially dried material is added to an aqueous suspension of 2,5-dihydroxy-1,4-dithiane (1 g) in 50 mL of water, which had been previously stirred with either Mg(OAc)$_2$ or NaOAc for 20 minutes at 30° C. This combined aqueous suspension is stirred between 30° C. and 60° C. for 24 hours. The modified cellulose is isolated by filtration, and washed with 50° C. water three times. The material can be used wet. The material can be dried by placing in an oven at 80° C. for 24 hours. It can also be dried in the filter funnel by washing with acetone two times, placed in a round bottom flask, which is subsequently placed on a rotary evaporator (rotovap) and dried.

Example 7—Modified Microcrystalline Cellulose

Microcrystalline cellulose (10 g), 2,5-dihydroxy-1,4-dithiane (1 g), APES (1.5 g), and Mg(OAc)$_2$ (0.25 g) are mixed together in a 250 mL round bottom flask containing 75 mL of water, and stirred for 24 hours between 30° C. and 60° C. Modified cellulose is isolated by filtration and used wet, or dried as described in previous Examples.

Example 8—Modified microcrystalline cellulose from 7-(prop-3-triethoxysilane)-(2,5-dithia-7-aza-bicyclo[2.2.1]heptane APES (2 g) and 2,5-dihydroxy-1,4-dithiane (1 g) are stirred in 95% ethanol (50 mL) containing Mg(OAc)$_2$ or NaOAc (0.5 g) dissolved in water (2 mL) and heated between 30° C. and 60° C. for 24 hours. Most (70-80%) of the ethanol is removed on a rotovap, the reaction is partitioned between ethyl acetate and water (50:50). The aqueous layer is extracted 3 times with ethyl acetate, the organic extracts are combined, dried with Mg(SO4)2, filtered and rotovaped to leave 7-(prop-3-triethoxysilane)-(2,5-dithia-7-aza-bicyclo[2.2.1]heptane as an oil.

Microcrystalline cellulose (10 g) is stirred in toluene (50 mL) and 7-(prop-3-triethoxysilane)-(2,5-dithia-7-aza-bicyclo[2.2.1]heptane (2 g) is added to this slurry. The reaction is heated to reflux (condenser attached) from for 6 hours. The cooled reaction is filtered, the modified microcellulose is washed (×2) with hot water followed by acetone (with filtering). The material is ready for use, but can be dried further under vacuum in a suitable round bottom flask (RBF). This reaction can be done using water as solvent also.

Figure 12A:
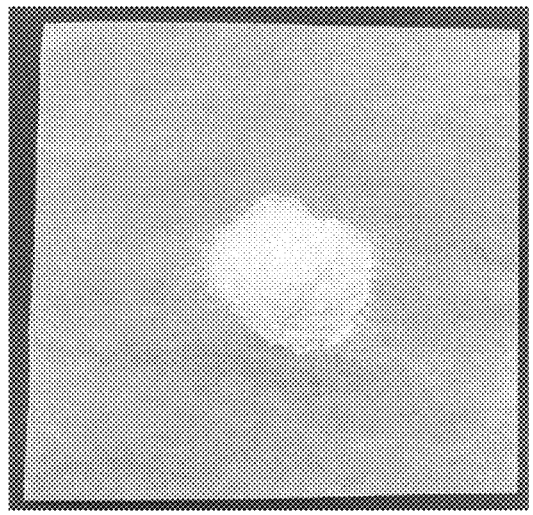
FIGS. 12A and 12B depict microcrystalline cellulose before (FIG. 12A) and after APES-dithiane modification (FIG. 12B)
Figure 12B:
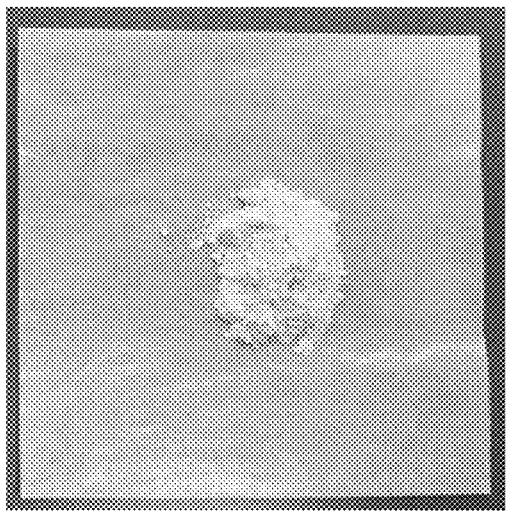

Photographs of unmodified and APES-dithiane modified microcrystalline cellulose are shown in FIGS. 12A and 12B, respectively.

Materials made via Examples 5-8 are indistinguishable. The above procedures can be applied using various grades of cellulose, as well as cellulose directly from the product-line of a pulp mill. All materials have the distinguishing chemical reducing properties when tested using I$_2$ in dry column chromatography (DCC) as described in FIG. 8, and AuCl$_3$ in water as qualitative tests.

APES dithiane modification of pulp-derived cellulose (FIGS. 9A-C) and cotton can be achieved using the same methodology as described in Examples 5-8. The materials all give positive I$_2$ tests using DCC. The modified pulp-derived cellulose has a high reducing ability towards gold 3+, as is described in material characterization.

Example 9—Modified Chitosan

Figure 13A:
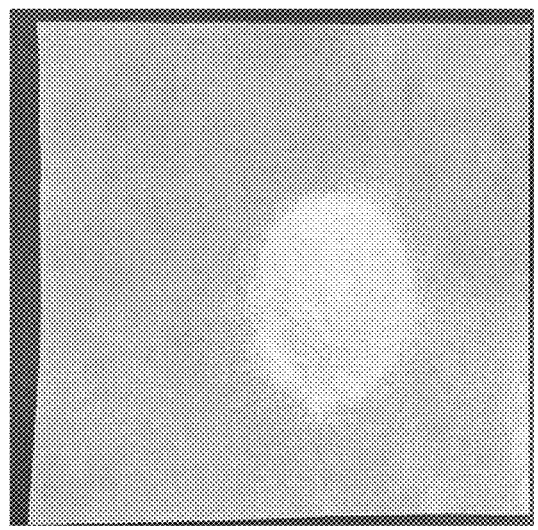
FIGS. 13A and 13B depict chitosan before (FIG. 13A) and after APES-dithiane modification (FIG. 13B).
Figure 13B:
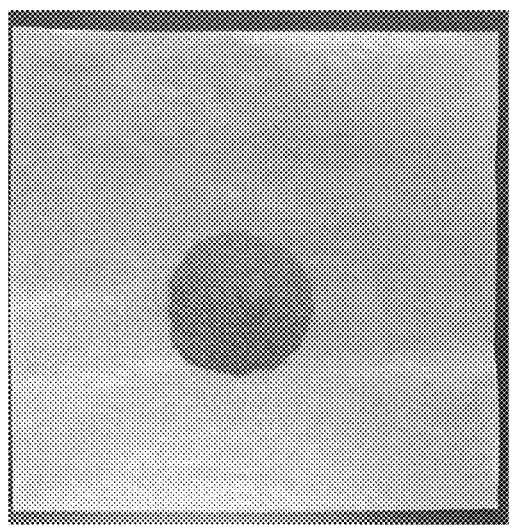

Chitosan (90 g) is placed in a 2 litre beaker along with a stir bar. Water (1300 mL) is added and stirring is started. An aqueous suspension of 2,5-dihydroxy-1,4-dithiane (5 g) containing 1 g of Mg(OAc)$_2$ is added to the chitosan suspension in the 2 litre beaker. The stirred suspension is heated to 85° C. on a hot plate for 2 hours. The material is filtered through a sintered glass funnel and washed three times with hot water (90° C.). The material can be used damp for aqueous applications. The material can be rinsed in the sintered glass funnel two times with acetone and allowed to air dry. The modified material has a slightly off-white color, as shown in FIG. 13B, compared to unmodified chitosan (FIG. 13A).

Example 10—Modified Polystyrene

4-Vinylbenzylamine (Feng, Designed monomers & Polymers 2017) is added dropwise to an aqueous suspension of 2,5-dihydroxy-1,4-dithiane being stirred with a 10% catalytic amount of NaOAc. After 3 hours the reaction mixture is extracted with ethylacetate, the organic layer is dried with MgSO4, filtered, and rotovaped to yield 7-(4-vinylbenzene)methyl-2,5-dithia-7azabicyclo[2.2.1]heptane. This monomer is polymerized either neat or in various proportions with styrene, in the presence of azobisisobutyronitrile (AIBN) at 35° C. to produce a solid, waxy material. The material is soluble in chloroform and 1H NMR reveals the presence of the 2,5-dithio-7-azabicyclo[2.2.1]heptane unit, together with the backbone of the polymer.

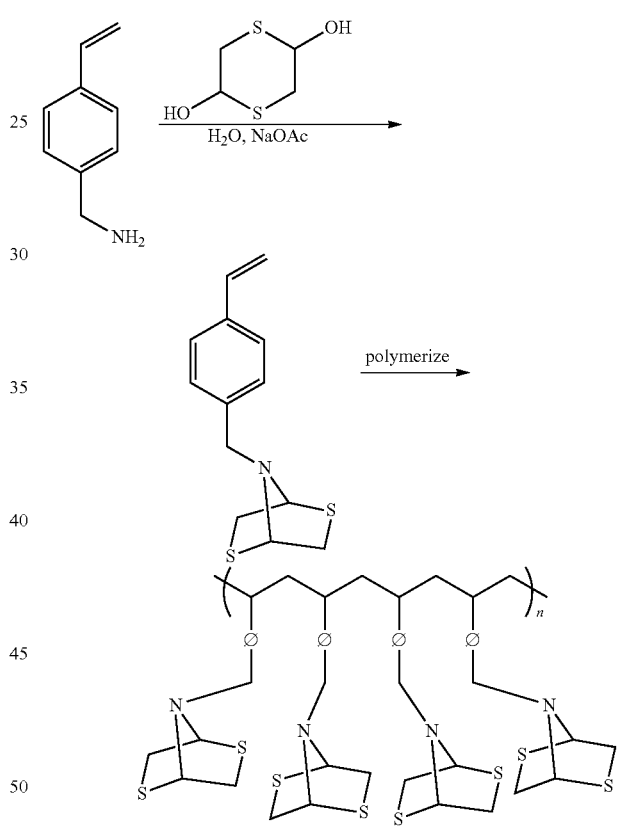

Scheme 7 depicts a general reaction scheme for the production of redox active polystyrene material from a 1,5-dithio-7-azabicyclo[2.2.1]heptane-containing monomer.

Example 11—Modified Poly(Ethyleneimine)

Poly(ethyleneimine) (PEI, Mw 600,000-1,000,000) (3 mL, 50% aqueous solution) is added to a stirred aqueous suspension of 2,5-dihydroxy-1,4-dithiane (1 g) which has been stirred with magnesium acetate (0.25 g) in 200 mL of water. An immediate white precipitate forms. Water is poured off from the cooled reaction and the solid material is washed with acetone, and pumped to dryness to yield a yellowish solid. This solid has a large capacity to decolorize purple I$_2$ in DCM. It also reduces aqueous gold 3+ to nanoparticles and larger particles.

Example 12—Modified Poly(Ethyleneimine)

Poly(ethyleneimine) (PEI, Mw 25,000, branched) (1 mL, 100% pure) is added to a stirred suspension of 2,5-dihydroxy-1,4-dithiane (1 g) which has been stirred with magnesium acetate (0.25 g) in 100 mL of water, under nitrogen. The solution produced an immediate precipitate, which re-dissolved within a few minutes. After an hour of stirring, water was evaporated under reduced pressure to produce an oil. Proton NMR in D20 resulted in a spectrum very similar to that shown in FIG. 15, indicating the presence of 2,5-dithio-7-azabicyclo[2.2.1]heptane units. The oil in water decolorized a purple I$_2$ solution in DCM that was added to it, to a great extent.

Example 13—Modified Starch

Starch (potato or corn, 10 g) is stirred in water (100 mL) with 2,5-dihydroxy-1,4-dithiane (1 g), (3-aminopropyl)triethylsilane (1.5 g), and Mg(OAc)$_2$ (0.25 g) for 6 hours at 40° C. The material is filtered, washed with hot water and acetone. This modified starch material gave a positive I$_2$ test.

Example 14—Modified Agarose

Agarose (4 g) is stirred in water (75 L) with 2,5-dihydroxy-1,4-dithiane (0.5 g), (3-aminopropyl)triethylsilane (0.75 g), and Mg(OAc)$_2$ (0.20 g) for 6 hours at 40° C. The material is filtered, washed with hot water, followed by acetone and dried.

Materials made in Examples 9, 10, 11, 12, 13, and 14 all exhibit reducing properties. All materials exhibit the distinguishing chemical reducing properties when tested using I$_2$ in dry column chromatography (DCC) and AuCl$_3$ in water as qualitative tests.

Example 15—Modified Paper

Fischer Scientific brand filter paper (P8) or laboratory grade paper towel, was cut into pieces and stirred in a 100 mL beaker containing water (20 mL), 2,5-dihydroxy-1,4-dithiane (0.1 g), Mg(OAc)$_2$ (0.05 g) and APES (0.15 g) with heating for 1 hour. The paper was rinsed with hot water (2×20 mL) followed by acetone. The resultant paper turned brown with a drop of I$_2$ (untreated filter paper stained purple).

Example 16—Modified Celite™

Celite™ 521 (Aldrich) (5 g) was stirred and heated in water (100 mL) containing 2,5-dihydroxy-1,4-dithiane (1 g), APES (1.5 g), and Mg(OAc)$_2$ (0.5 g) for 2 hours. The material was collected by filtration, washing with hot water followed by acetone. This material was very reactive towards the I$_2$ test, whereas Celite™ modified with just APES allowed the purple color to pass cleanly through the material.

Example 17—Modified Polyallylamine

Polyallylamine hydrochloride (3 g) was diluted in water (25 mL) and then added to a stirred suspension of 2,5-dihydroxy-1,4-dithiane (1 g) in water, containing magnesium acetate (0.25 g) in 100 mL of water. The reaction was stirred for an additional hour. Removal of water under reduced pressure resulted in an oil. Proton NMR of the oil, dissolved in D20 showed clearly incorporation of the 2,5-dithio-7-azabicyclo[2.2.1]heptane units. Peaks at 5.1, 3.3 and 3.1 ppm, although broad (because of the size of the polymeric molecules), had the appropriate chemical shifts and integration expected for the azabicyclic system.

Figure 14:
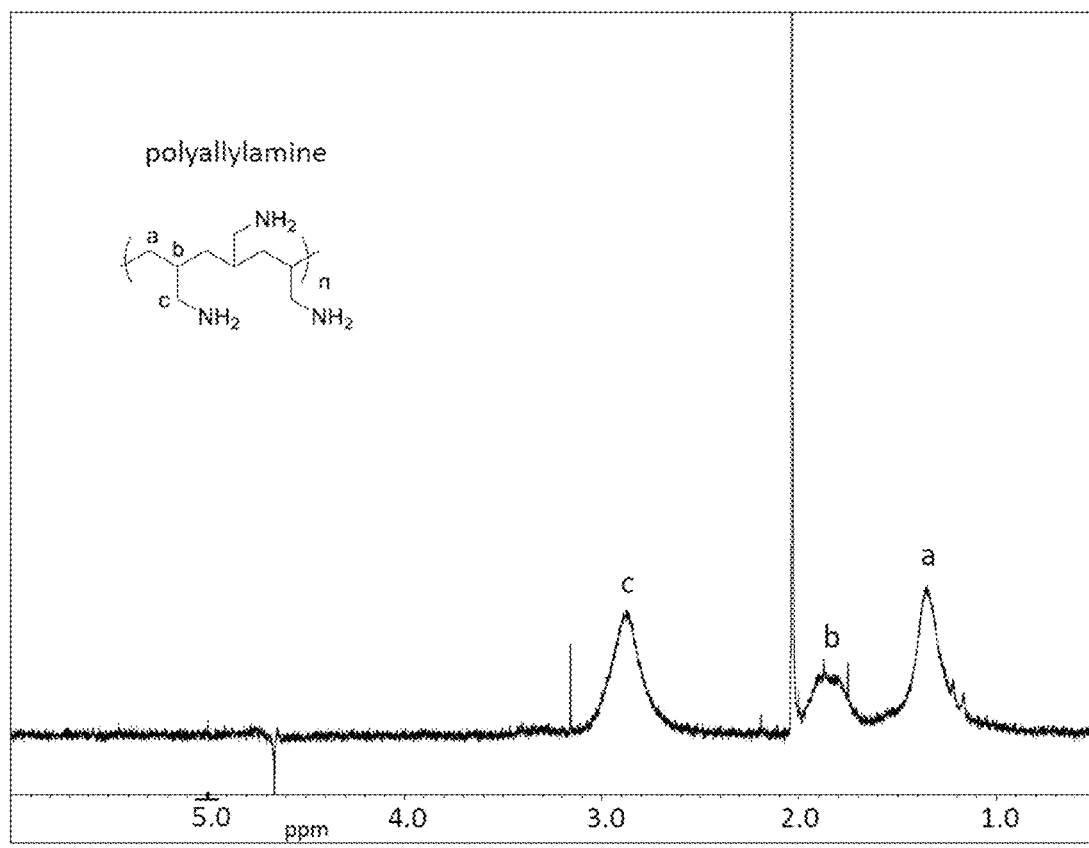
FIG. 14 depicts the proton NMR spectrum of pollyallylamine hydrochloride, average Mw=17,500, in D20, with solvent suppression at 4.6 ppm.
Figure 15:
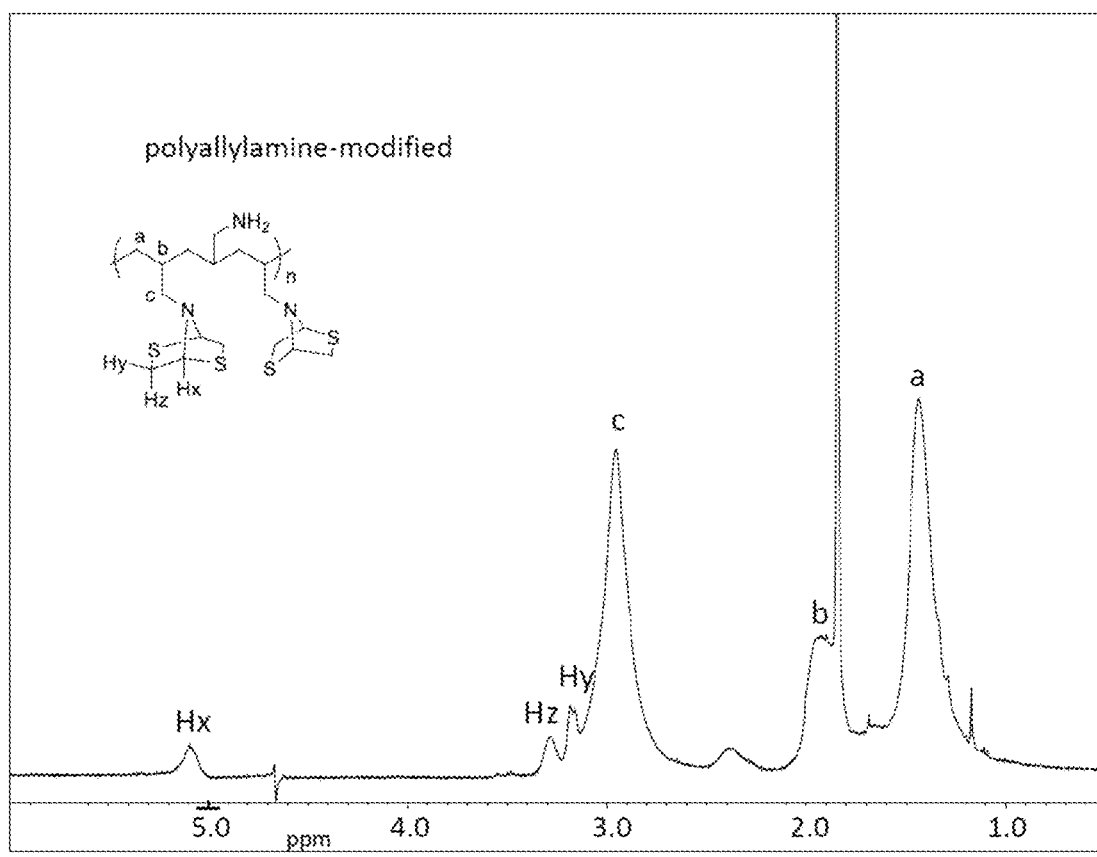
FIG. 15 depicts the proton NMR spectrum 2,5-dithio-7-azabicyclo[2.2.1]heptane modified polyallylamine (average Mw=17,500) in D20 with solvent suppression at 4.6 ppm. All peaks are broad because of the size of the polymeric molecules. In small molecules, protons Hx typically occur at 5.1 ppm as a doublet, split by Hy. Protons Hz typically appear around 3.3 ppm as a doublet, geminally split by Hy. Protons Hy typically occur at 3.1 ppm as a doublet of doublets, split by Hx and geminally split by Hz. The Hx, Hy and Hz peaks are integrated in a 1:1:1 ratio exactly as expected, approximately 10% of the area of Hc, indicating that not all of the $NH_2$ groups were modified in this sample.

To illustrate, FIGS. 14 and 15 are related to the functionalization of pollyamine hydrochloride, average Mw=17, 000. FIG. 14 is the solution phase proton NMR spectra of polyallylamine hydrochloride (PAH) in D20. The spectrum agrees with a published spectrum (M. A. Alkhabbaz et al./Fuel 121 (2014) 79-85). FIG. 15 is the proton NMR spectra of 2,5-dithio-7-azabicyclo[2.2.1]heptane modified polyallylamine. The second spectrum shows clearly the peaks at the expected chemical shift for protons labelled Hx, Hy and Hz.

Example 18—Modified Model Protein—Ubiquitin

A proof-of-principle that materials containing primary amino groups in macromolecules can be modified with 2,5-dihydroxy-1,4-dithiane to produce 2,5-dithio-7-azabicyclo[2.2.1]heptane modified material was undertaken with a protein. As a model protein, the modification of the lysine groups in ubiquitin, a relatively small protein having neutral molecular mass of 8564.8448, was examined. The amino acid sequence of ubiquitin is MQIFVKTLTGKTITLEVE-PSDTIENVKAKIQDKEGIPPDQQRLIF-AGKQLEDGRTLSDYNI QKESTLHLVLRLRGG (SEQ ID NO:1), indicating the presence of 7 lysine residues.

Modified ubiquitin was obtained as follows: A 50 µL sample of ubiquitin (0.06 M) in 100 µL of water containing 5 equivalents of 2,5-dihydroxy-1,4-dithiane and a catalytic amount of magnesium acetate was stirred for 2 hours at 30° C. Mass spectral analysis was performed on a linear quadrupole ion trap (LTQ) mass spectrometer (Thermo-Fisher Scientific, San Jose, CA) using electrospray ionization.

Briefly, the sample was diluted 2-fold in methanol that was acidified with 0.1% formic acid. The sample was loaded into a 500 microliter glass syringe and infused into the ion source at 3 uL/min. Data was collected in positive ion mode over a mass range of 400-2000.

Figure 16:
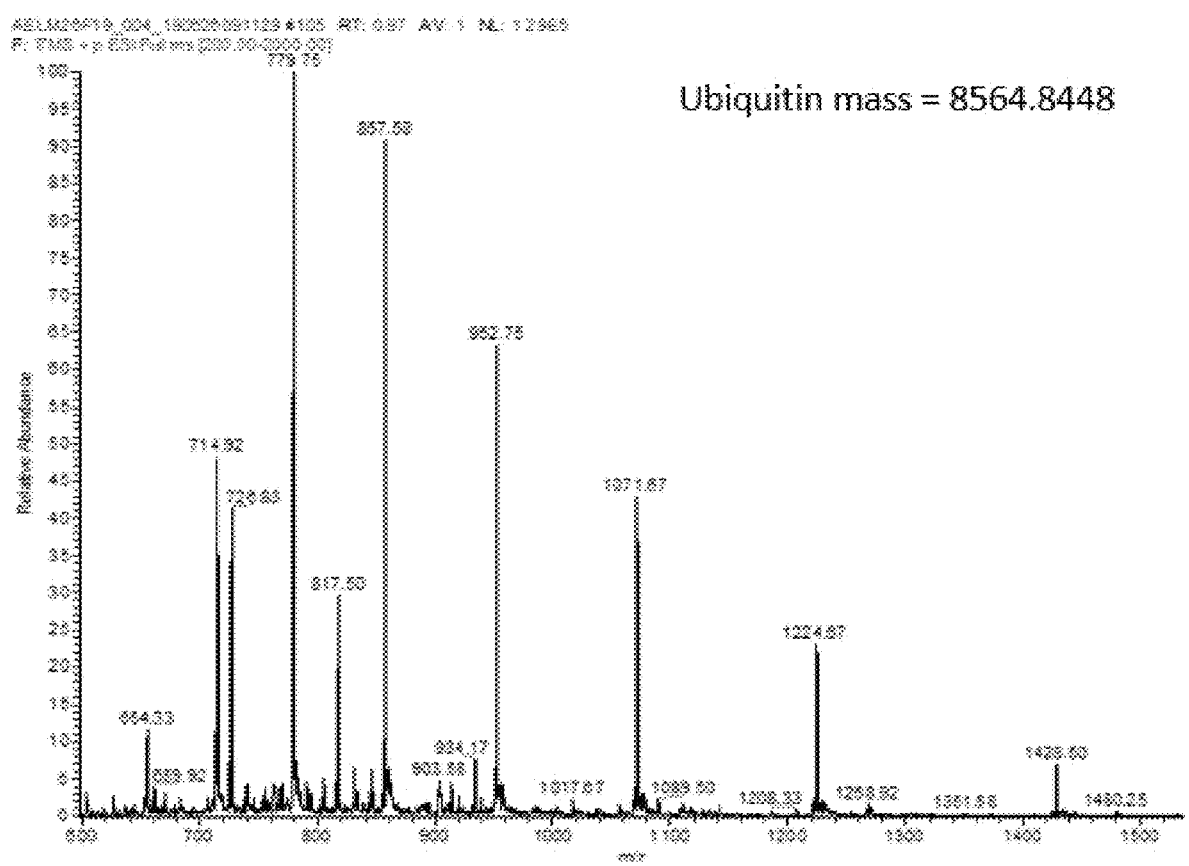
FIG. 16 depicts the mass spectrum of unmodified ubiquitin, neutral molecular mass=8564.8448 Daltons. Peaks at 1428, 1224, 1071, 952, 857, and 779 represent species with increasing mass-to-charge ratios with charges of +6, +7, +8, +9, +10 and +11 respectively. For example, 8564.8448+6 (the addition of 6 protons to give a positive charge of +6)=8570.84. 8570.84/6=1428.5, the peak to the right of the spectrum.
Figure 17:
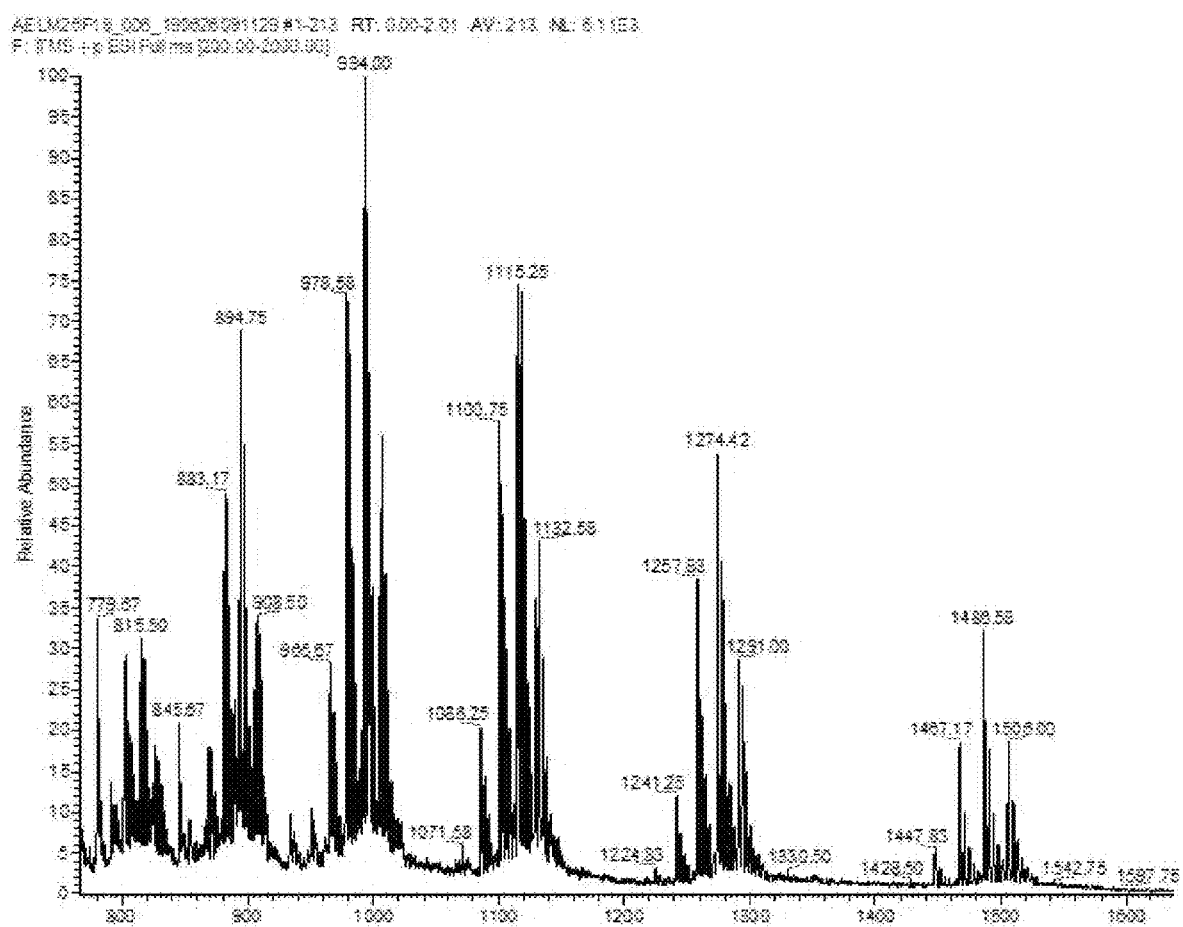
FIG. 17 depicts the mass spectrum of ubiquitin that has been partially modified by 2,5-dithio-7-azabicyclo[2.2.1] heptane units. Each 2,5-dithio-7-azabicyclo[2.2.1]heptane modification of a lysine (or the terminal amino group) increases the mass by 116 ($C_4H_6S_2$ —2). Consider the peaks centered around 1500. The peak at 1428.5 is barely visible, indicating that there is very little unmodified ubiquitin left in the sample. The peak to the right of 1428.5 is 1447.83. The difference between the two is 19.33. 19.33×6=116. The peak to the right of 1447 is 1467.17. The difference is 19.34. 19.34×6=116. The peak at 1486.58 is the addition of a $3^{rd}$ 2,5-dithio-7-azabicyclo[2.2.1]heptane unit. The peak at 1506.00 is the species with a $4^{th}$ addition of a 2,5-dithio-7-azabicyclo[2.2.1]heptane unit.
Figure 18:
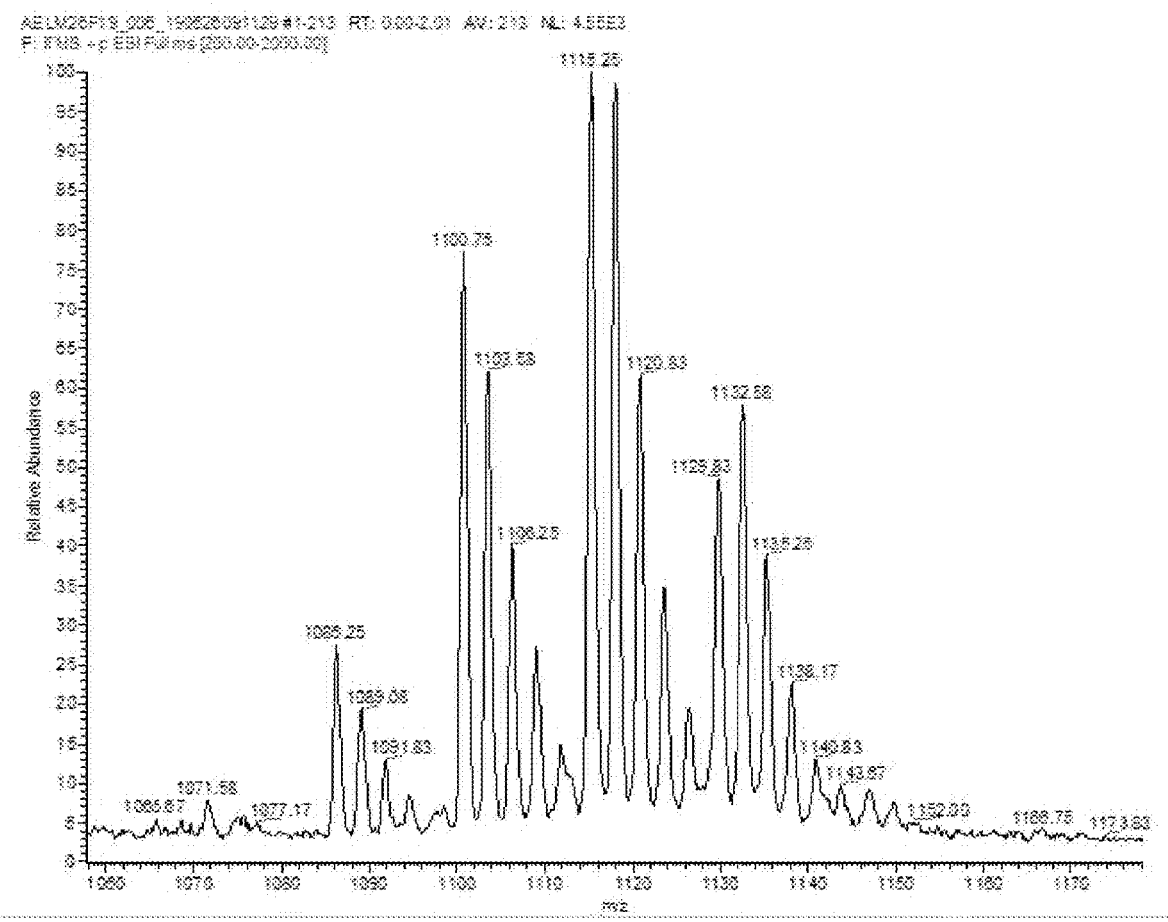
FIG. 18 depicts an expansion of FIG. 17 centered around 1120 Daltons, which corresponds to protein molecules with a charge of +8 ((8564.8448+8)/8=1071.6). That 1071.58 peak being so small indicates very little of the unmodified protein left in solution. 1100.75−1086.25=14.5. 14.5× 8=116. From 1100.75 to 1115.25 is the addition of another 116 mass units.
Figure 19A:
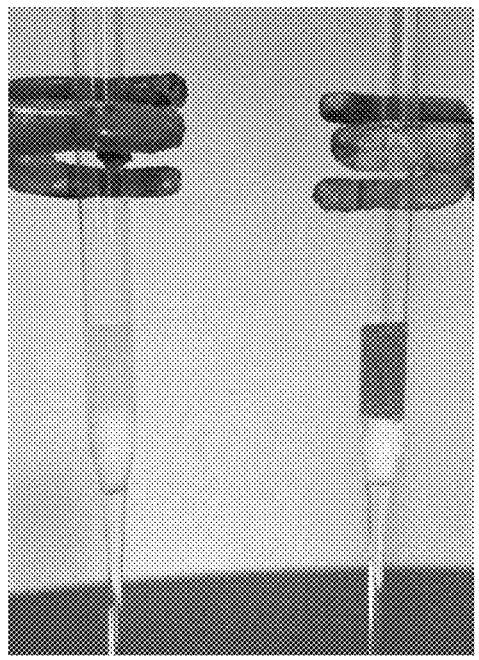
FIGS. 19A, 19B, 19C and 19D depict a series of 4 pictures of the Pasteur pipette test described in FIG. 8 using $I_2$ in DCM. Unmodified silica gel is on the left and APES dithiane modified silica gel is on the right.
Figure 19B:
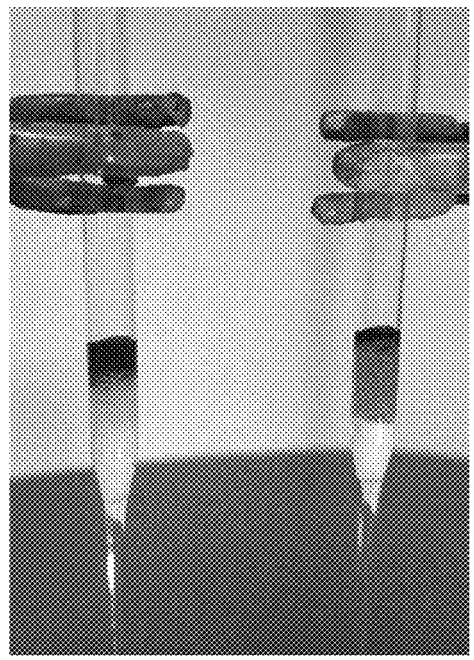
Figure 19C:
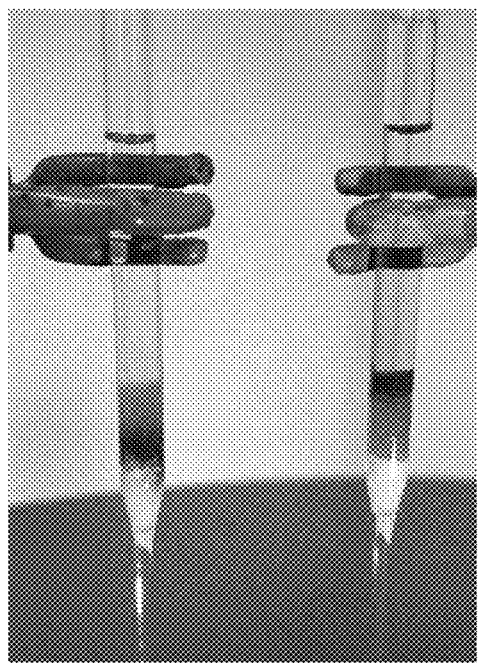
Figure 19D:
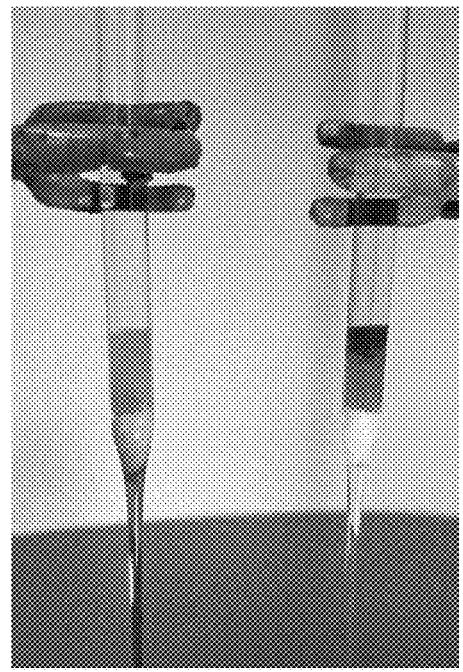

Spectra (FIGS. 16, 17, 18) show conclusively that the protein is being modified by consecutive additions of units containing 116 mass units. More particularly, FIGS. 16, 17 and 18 are high resolution Mass Spectra showing clearly the 2,5-dithio-7-azabicyclo[2.2.1]heptane functionalization of the protein ubiquitin. The Mass Spectra show that stirring ubiquitin, a small protein that contains 7 lysine residues (that terminate in NH$_2$ groups) with Mg(OAc)$_2$ and 2,5-dihydroxy-1,4-dithiane in water results in the exact mass increase expected for adding $C_4H_6S_2$–2H=116 units (the 2,5-dithio-7-azabicyclo[2.2.1]heptane unit minus the 7-azo nitrogen and the 2 hydrogens that belonged to the lysine residues) to 4 of the lysine residues, over 2 hours of stirring at 30° C.

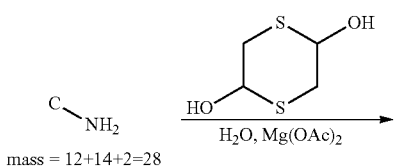

mass = 12+14+2=28

43

-continued

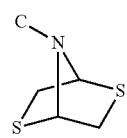

mass = 12+14+48+6+64 = 144

The above diagram indicates an increase in mass of a primary amine of 116 amu (144−28=116). This is exactly what is observed in the mass spectra shown in FIGS. 16, 17, 18.

Apart from the reductive properties that would be imparted to such material, selective functionalization of the terminal amino group and lysine residues of a peptide or protein provides an additional technology for peptide or protein characterization and proteomics analysis, by mass spectrometry. Trypsin cleaves selectively after lysine or arginine. Selective blocking of lysine would be highly desirable. The present embodiment achieves this.

Example—19 Redox Active Polyesters and Polyamides

Redox active polyesters and polyamides can be made according to the general polymerization/condensation scheme described in Schemes 5a and 5b. Amine monomers can be transformed into the 2,5-dithio-7-azabicyclo[2.2.1] heptane system by methods disclosed herein. These bicyclic dithiane monomers are heated to 100° C. in the presence of suitable diols or diamines for 24 hours to produce polymeric material. Copolymerization occurs by including a co-monomer in the desired ratio.

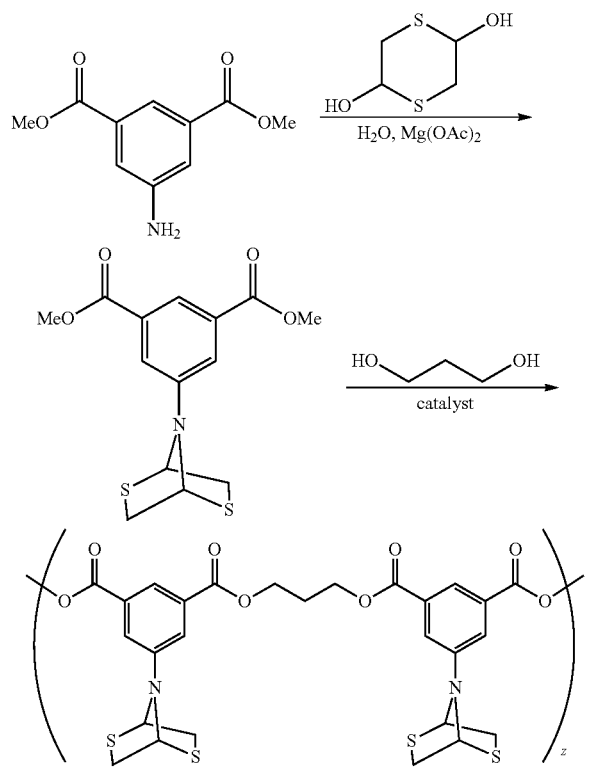

44

Scheme 8 depicts the synthesis of a redox active polyester starting from dimethyl-5-aminoisophthlate and 1,3-propanediol. The 2,5-dithio-7-azabicyclo[2.2.1]heptane modified dimethyl-5-aminoisophthalate is synthesized cleanly by the method disclosed herein. It can be polymerized directly with 1,3-propanediol as condensing agent. It can be co-polymerized with 1,3-propanediol as condensing agent and dimethyl isophthalate as a spacer in ratios from 1:1 to 1:100 (monomer to co-monomer). The resulting copolymer would have the monomer and co-monomer randomly distributed.

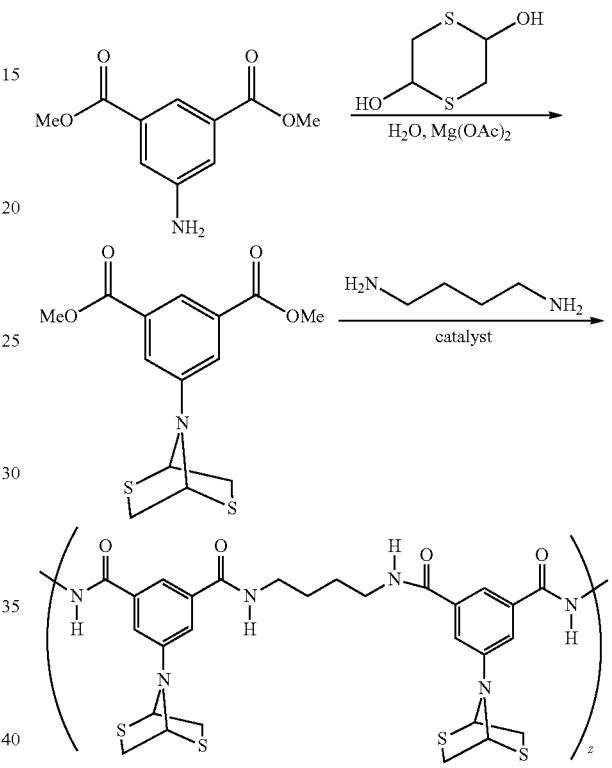

Scheme 9 above depicts the synthesis of a redox active polyamide starting from dimethyl-5-aminoisophthlate and 1,4-butanediamine. The 2,5-dithio-7-azabicyclo[2.2.1]heptane modified dimethyl-5-aminoisophthalate can be polymerized by hearting in the presence of 1,4-diaminobutane as the condensing agent. It can be copolymerized with 1,4-diaminobutane as condensing agent and dimethyl isophthalate as a spacer in ratios of 1:1 to 1:100 (functionalized to unfunctionalized). The functionalized and unfunctionalized units would be randomly distributed.

Example 20—Applications of Redox Active Materials

The redox active materials obtained according to the above Examples may for example be used for gold extraction subsequent to a gold ore leaching process. The materials are particularly compatible with the thiosulfate leaching process.

Figure 8:
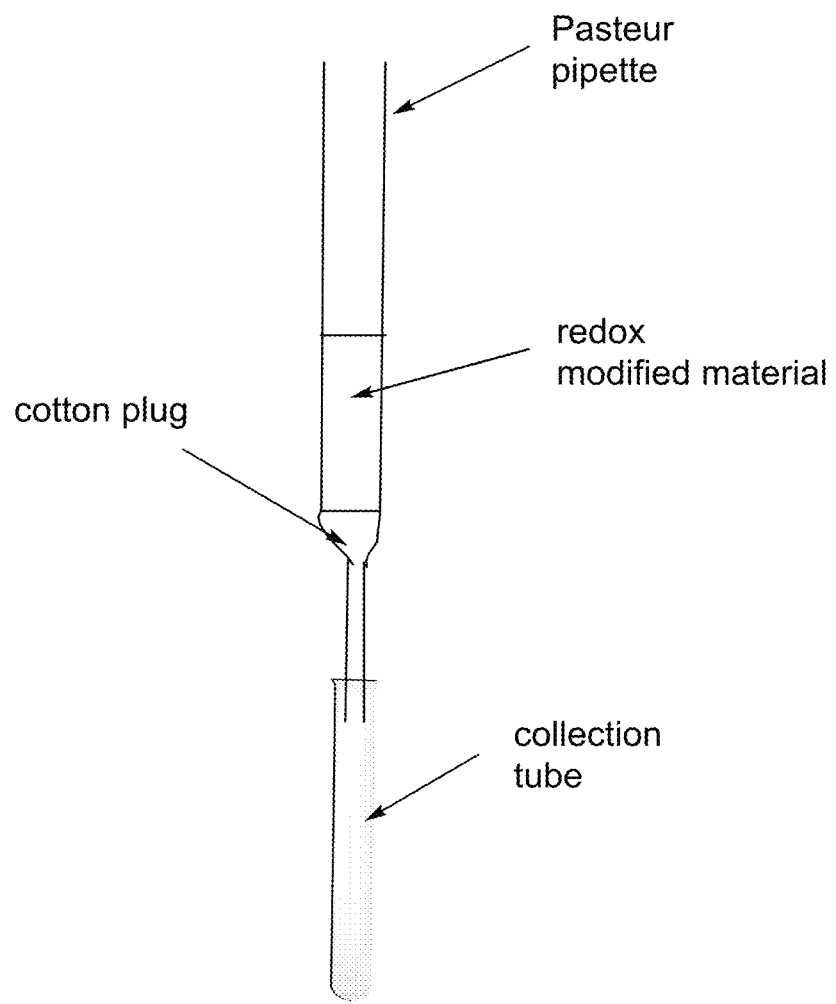
FIG. 8 depicts a typical setup using a Pasteur pipette and an iodine ($I_2$) solution in dichloromethane (DCM) for testing the redox nature of modified material. The same setup can be used to show $AuCl_3$ being reduced to $Au^0$ in aqueous solution. Typical results of such $I_2$ tests are depicted in FIGS. 19A-D.

To test the redox nature of modified materials, a typical set up using a Pasteur pipette and an iodine solution in dichloromethane, as shown in FIG. 8, when the iodine solution is for example tested on unmodified cellulose, the purple iodine solution runs straight through the unmodified cellulose. In contrast, when the iodine solution is tested on modified cellulose (i.e. redox active material), the iodine solution gets reduced to iodide which then is combined with unreduced iodine to produce brown triiodide ($I_3^-$) which sticks to the top of the column electrostatically.

Figure 9A:
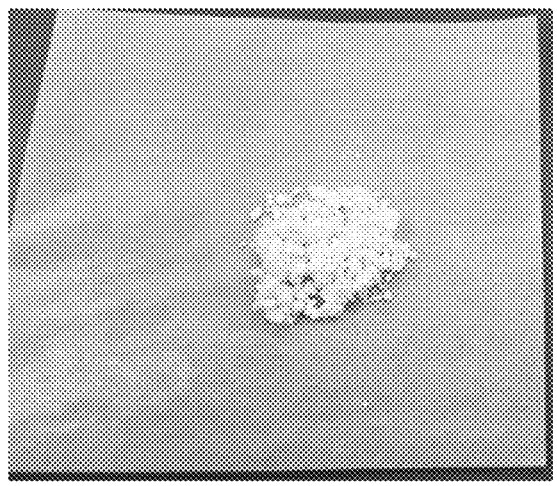
FIGS. 9A, 9B and 9C depicts pulp-derived cellulose before modification (FIG. 9A), after APES-dithiane modification (FIG. 9B) and with gold nanoparticles adsorbed to it (FIG. 9C) having reduced an aqueous solution of $AuCl_3$.
Figure 9B:
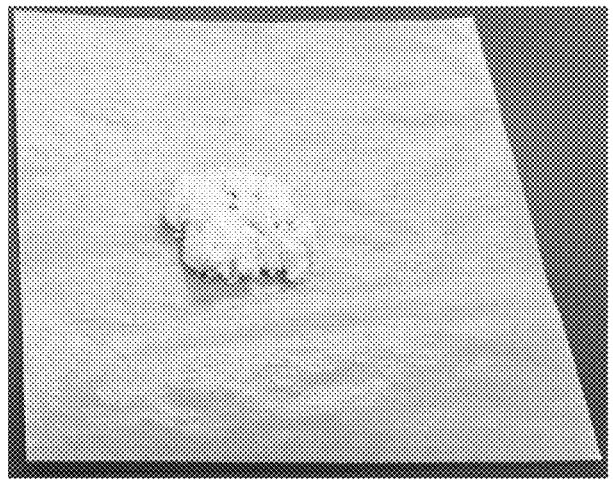
Figure 9C:

The same setup can be used to show $AuCl_3$ being reduced to $Au^0$ in aqueous solution. As shown in FIGS. 9A-C, when tested on modified cellulose (FIG. 9B), gold chloride is reduced to gold nanoparticles which are adsorbed to the modified cellulose (FIG. 9C). The gold chloride nanoparticles bind to un-oxidized 1,5-dithio-7-azabicyclo[2.2.1] heptane units of the modified cellulose, consistent with our previous finding that the 1,5-dithio-7-azabicyclo[2.2.1]heptane unit has an affinity for elemental gold (S. Ramsaywack et.al. J. Phys. Chem. C 2012, 116, 7886-7896).

Other suitable modified materials that may be used to adsorb metallic gold include modified microcrystalline cellulose (FIG. 12B), modified chitosan (FIG. 13B) and modified poly(ethyleneimine) (PEI).

Example 21—Material Characterization

The redox materials described in the above examples have been characterized by a variety of physical measurements, including solid state 13C NMR, liquid phase 1H NMR, scanning electron microscope imagining (SEM), and energy dispersive x-ray spectroscopy (EDS). Considering a peptide or protein to be a material, or macro-molecule, high resolution mass spectrometry has been used to show unequivocally that primary amines on such a macro-molecule can be selectively functionalized with the 2,5-dithio-7-azabicylo[2.2.1]heptane unit as is being claimed.

Infrared spectroscopy was found not to be useful in characterizing these redox active materials.

It was determined that an important characterization tool of the functionality for these redox materials is their chemical reactivity with oxidizing agents such as iodine ($I_2$), and their reactions with aqueous gold chloride.

Silica gel is known to be covalently modified by APES in both water and toluene to yield a material with primary amines attached to the surface. Aminopropyl silica gel is commercially available. Reaction of these primary amines with 2,5-dihydroxy-1,4-dithiane in the presence of $Mg(OAc)_2$ or NaOAc is expected to produce the corresponding 2,5-dithio-7-azabicyclo-[2.2.1]heptane units. In the following sections we provide physical, spectroscopic and functional evidence that this is the case.

Solid state 13 C NMR spectra (ss13C spectra) using magic angle spinning (MAS) recorded on a sample of APES-bicyclicdithiane modified silica gel reveals that the 2,5-dithio-7-azabicyclo-[2.2.1]heptane unit is present on the solid material. The ss13C spectra is reproduced in FIG. 1. It shows clearly the characteristic peaks for the 3 carbons of the aminopropyl linker at 8.5, 21.2 and 42.3 ppm, in accordance with a previously published study (A. Goswami, A. K. Singh/Analytica Chimica Acta 454 (2002) 229-240). The 2 carbons of the bicyclic dithiane portion appear at 51.4 and 68.7 ppm, in agreement with a previous synthesis of small-molecule bicyclic dithianes (S. Ramsaywack et.al. J. Phys. Chem. C 2012, 116, 7886-7896).

Figure 3:
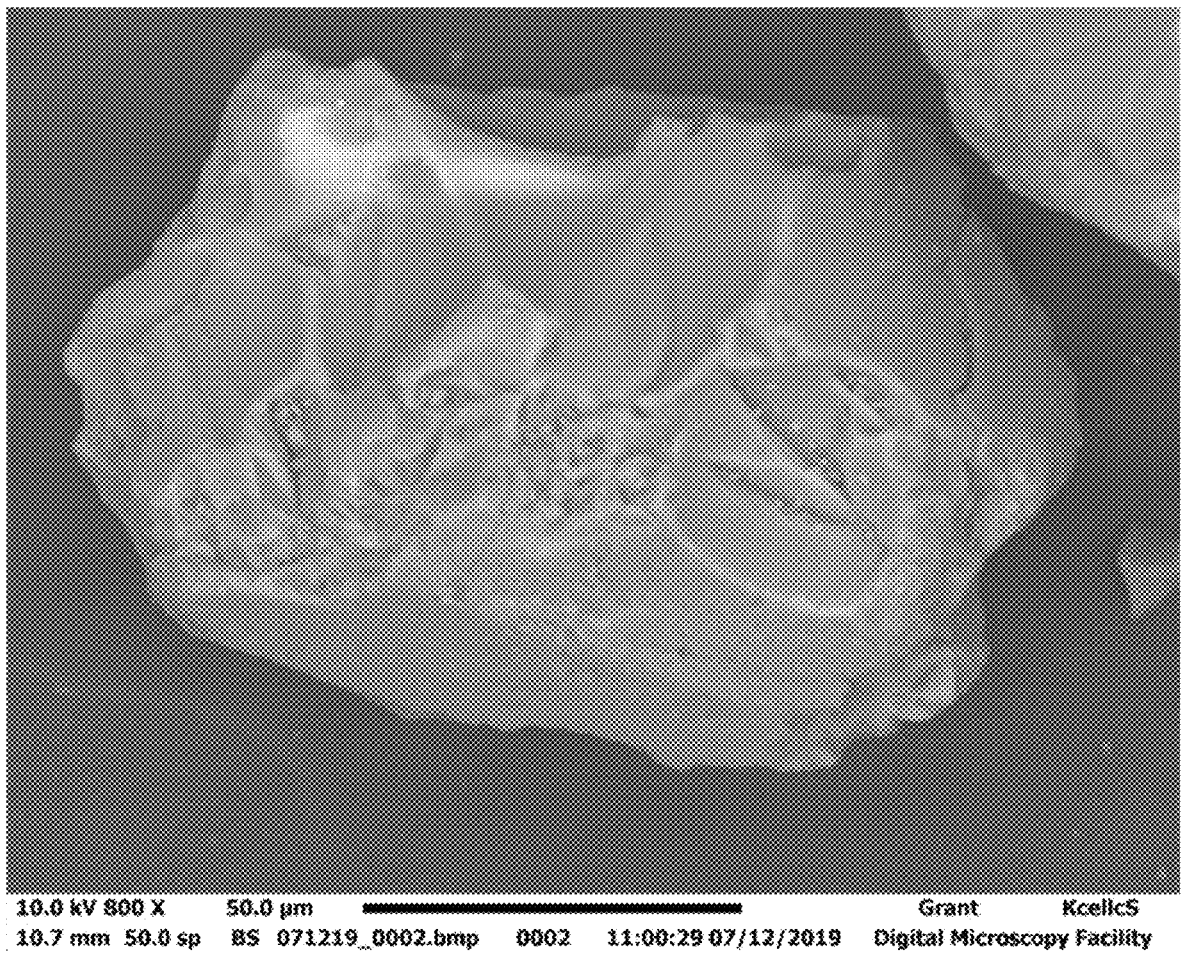
FIG. 3 depicts an SEM image of a silica gel particle that has been modified by APES/2,5-dithio-7-azabicyclo[2.2.1] heptane (APES-dithiane) units.
Figure 4:
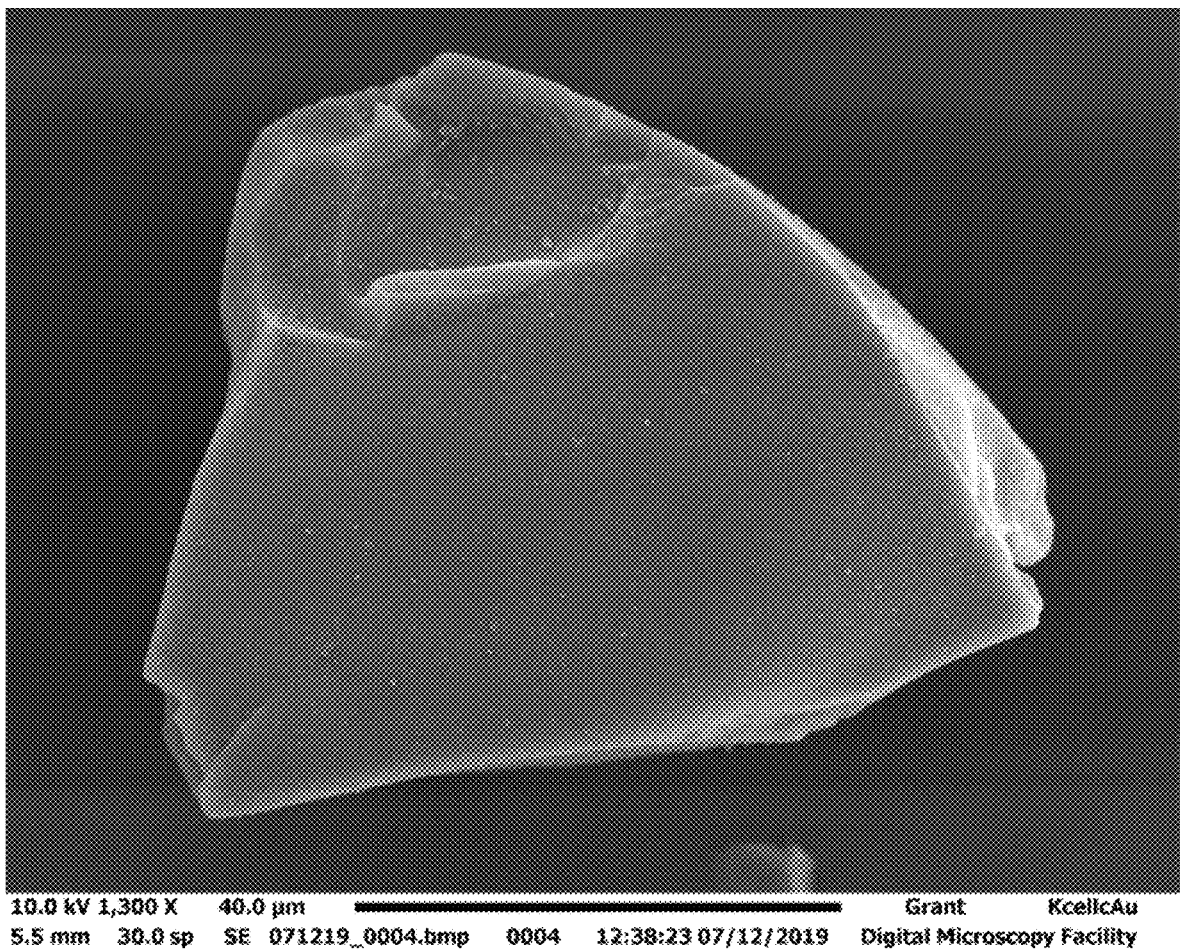
FIG. 4 depicts an SEM image of a silica gel particle modified with the APES/dithiane units. This material was placed in a Pasteur pipette as described FIG. 8, and treated with an aqueous 0.5% $AuCl_3$ solution. A reddish-purple band formed immediately, forming a band about 4 mm thick. This band was removed and subjected to SEM and EDS analysis. The bright spots are large Au nanoparticles (almost a micrometer) on the surface of the silica particle (see EDS spectrum in FIG. 7).
Figure 5:
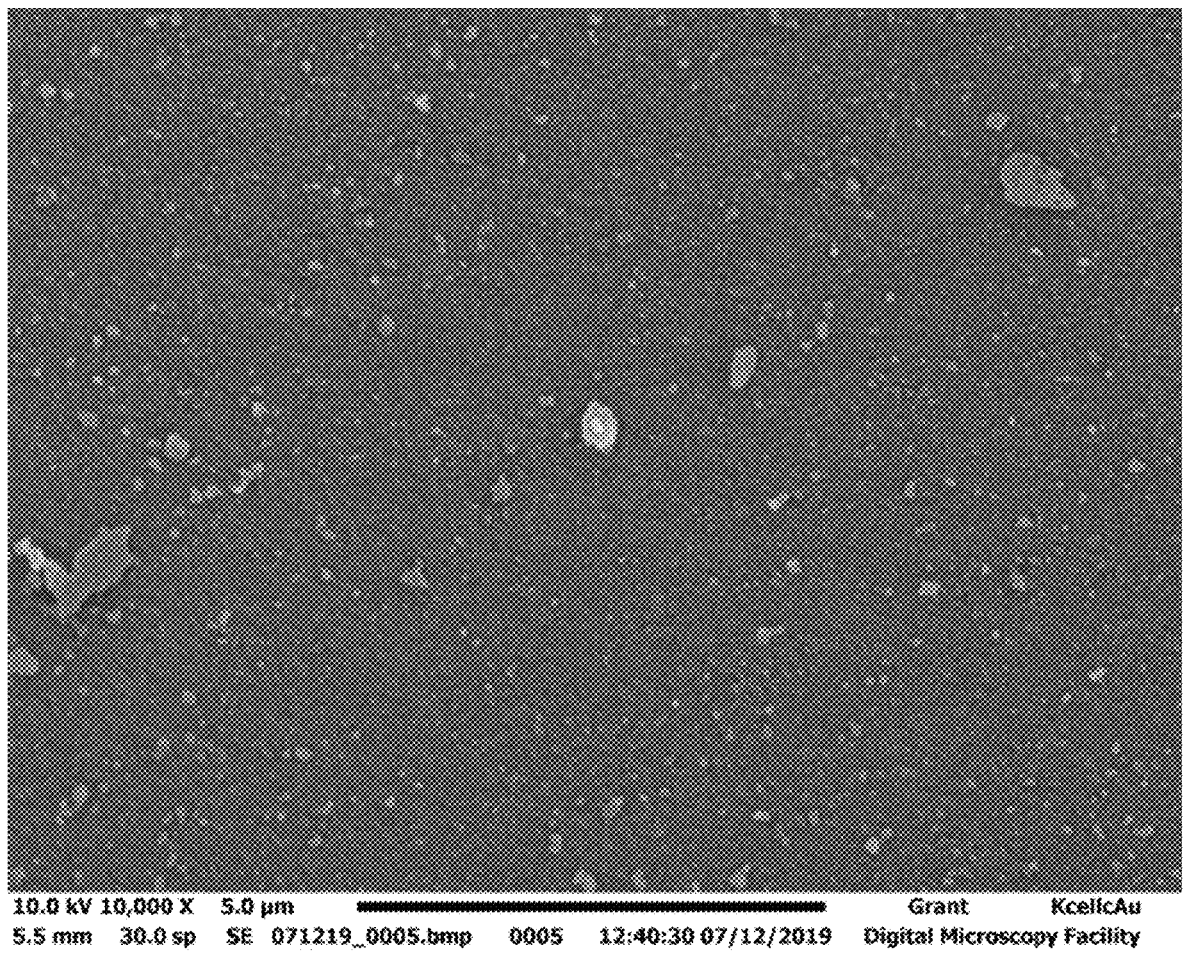
FIG. 5 depicts an expansion of the SEM image shown in FIG. 4 (approximately in the middle of the FIG.), showing gold particles. Zooming and focusing the X-ray beam on the center particle reveals it to be gold (FIG. 7).

The APES dithiane modified silica gel was further characterized by SEM and EDS. FIG. 3 is a SEM images of a 2,5-dithio-7-azabicyclo[2.2.1]heptane modified silica gel particle. FIG. 4 is an SEM image of a 2,5-dithio-7-azabicyclo[2.2.1]heptane modified silica gel particle that has been treated with aqueous $AuCl_3$. The bright spots are particles of gold that have formed on the surface of the silica as a result of reduction and aggregation. FIG. 5 is a close up of a portion of the particle in FIG. 4.

Figure 6:
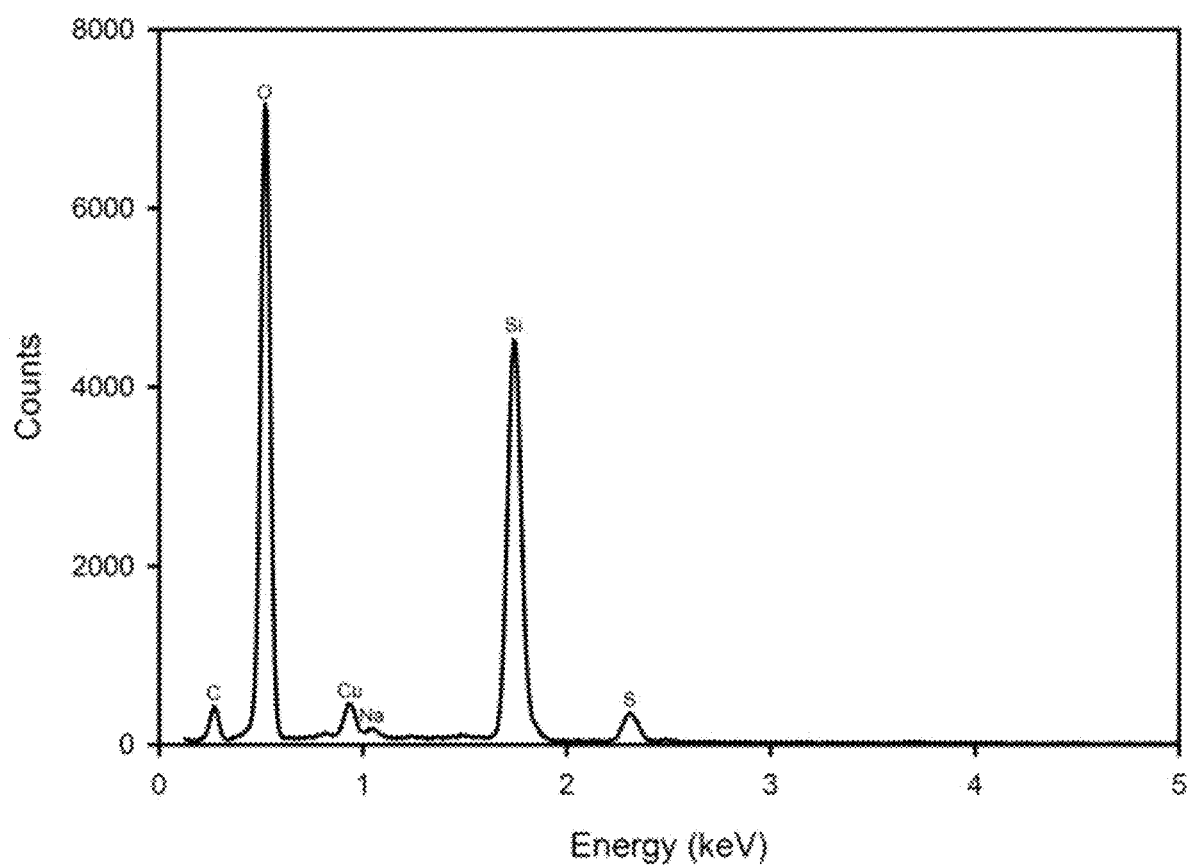
FIG. 6 depicts the EDS (energy dispersive x-ray spectroscopy) elemental composition spectra for silica gel modified with 2,5-dithio-7-azabicyclo[2.2.1]heptane units. The spectrum exhibits emissions characteristic of the presence of silica and oxygen, as well as carbon and sulfur, supporting the presence the 2,5-dithio-7-azabicyclo[2.2.1]heptane unit.

FIG. 6 is an EDS spectra showing the elemental composition of the modified silica gel before treatment with gold, It shows clearly the presence of silicon and oxygen, as well as sulfur and carbon, consistent with the presence of the 2,5-[2.2.1]heptane ring system.

Figure 7:
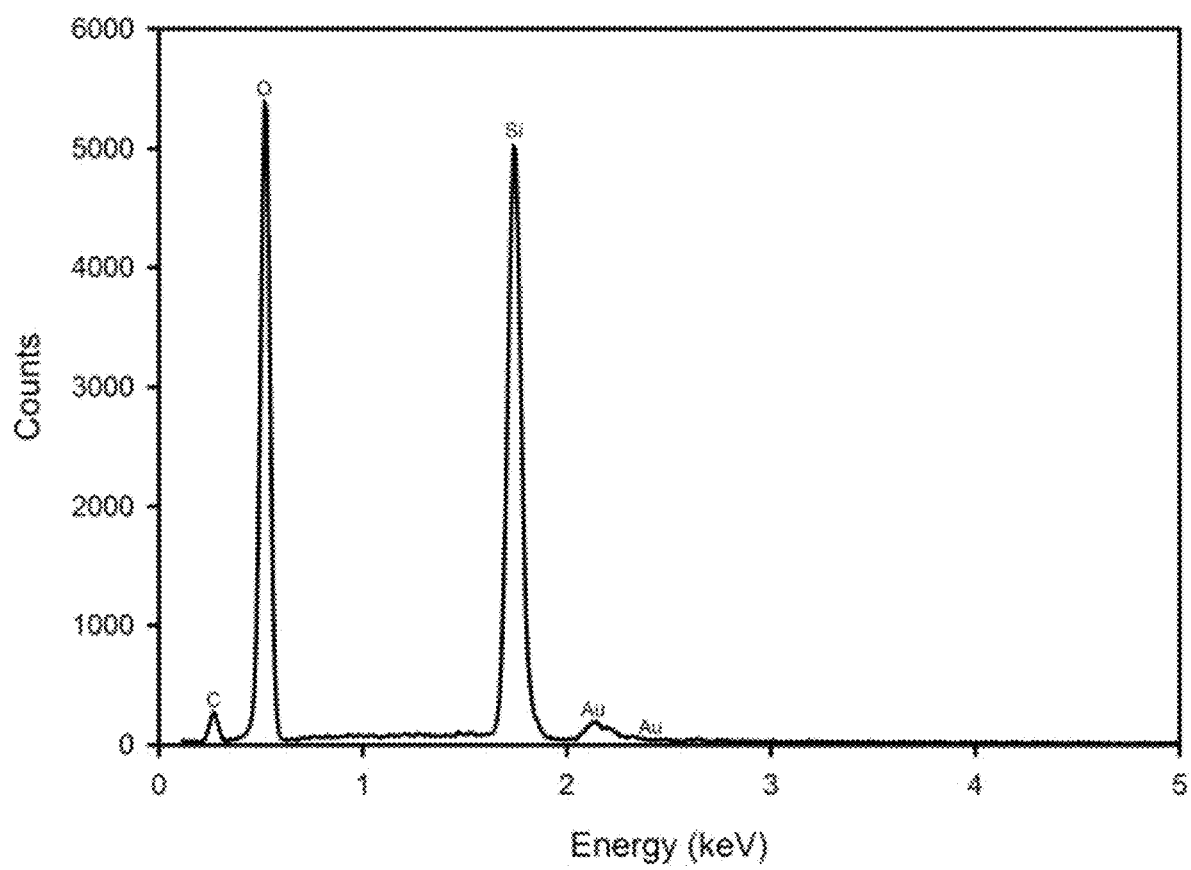
FIG. 7 depicts the EDS (energy dispersive x-ray spectroscopy) elemental composition spectra for silica gel modified with APES-dithiane units, and subsequently treated with 0.5% aqueous $AuCl_3$ in the Pasteur pipette experiment (FIG. 8). The top 4 mm of the column turns a reddish-purple, indicating the presence of gold nanoparticles. Spot focusing of the X-ray beam on the bright spots of the silica particles (FIG. 5 above) show emissions for silicon and oxygen, as well as gold.

FIG. 7 an EDS spectra of the APES-dithiane modified silica particle after treatment with gold chloride. The EDS spectrum in 7 shows clearly the presence of gold on the surface of the silica gel, consistent with the bright spots in FIGS. 4 and 5.

The modified silica gel reacts rapidly with dichloromethane solutions of $I_2$ as depicted in FIG. 8.

Cellulose is known to covalently bind (3-aminopropyl) triethoxysilane, and primary amines are known to form the 2,5-dithio-7-azabicyclo[2.2.1]heptane unit (S. Ramsaywack et.al. J. Phys. Chem. C 2012, 116, 7886-7896). No amount of washing abolishes the reducing property, indicating the 2,5-dithio-7-azabicyclo[2.2.1]heptane unit must be covalently attached to the cellulose.

Solid state 13 C NMR were recorded for APES-dithiane modified cellulose, but the carbon resonances for the modification could not be seen above the background of the cellulose peaks.

Figure 10:
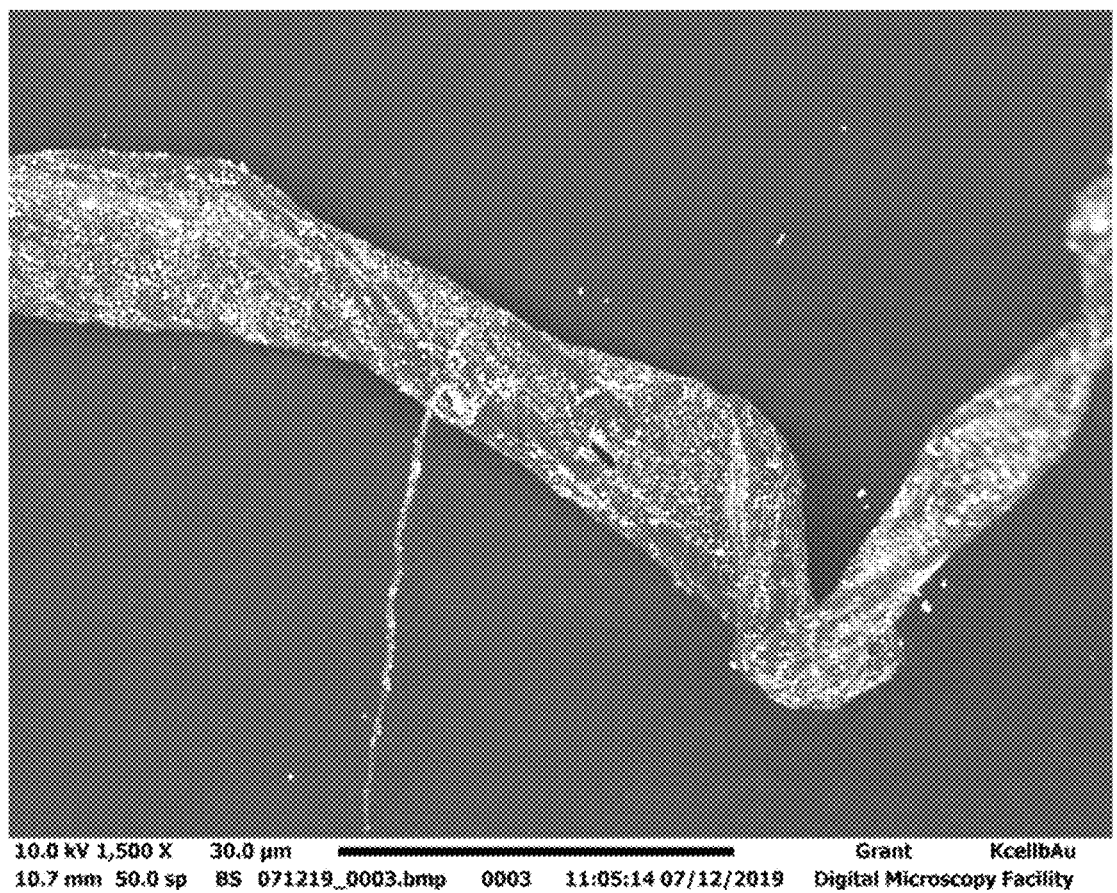
FIG. 10 depicts an SEM image of a strand of APES-dithiane modified pulp cellulose shown at FIG. 9B. The bright spots have been shown by EDS beam focusing to be gold particles on the surface of the cellulose.
Figure 11:
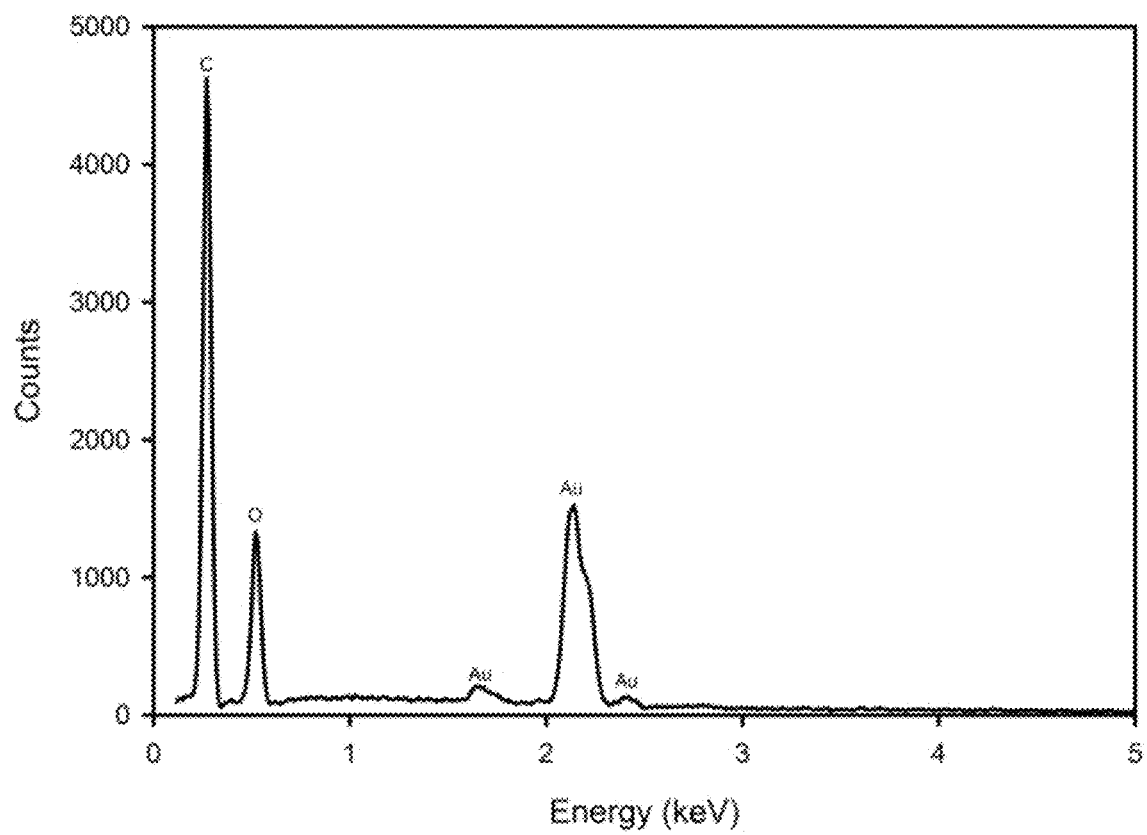
FIG. 11 is an image of the EDS spectrum of a particle of gold produced by reduction of an aqueous solution of gold 3+, followed by aggregation of gold atoms, by 2,5-dithio-7-azabicyclo[2.2.1]heptane modified pulp cellulose, shown FIG. 10.

FIGS. 10 and 11 pertain to 2,5-dithio-7-azabicyclo[2.2.1]heptane functionalized cellulose that has been reacted with gold chloride. FIG. 10 depicts a SEM image of a cellulose fiber taken on the sample shown in FIG. 9C showing many particles of gold on it. FIG. 11 is an EDS spectrum of a gold particle (much larger than a nanoparticle) that had fallen off the cellulose fiber onto the tape, that holds the sample in the SEM instrument.

Redox functionality of these redox active materials is illustrated by observing their reaction with an iodine solution in dichloromethane (DCM) (as illustrated in FIG. 8 and FIGS. 19A-D). A mini-column is prepared by adding half a gram of 2,5-dithio-7-azabicyclo-[2.2.1]heptane modified material from colloidal silica, silica gel, cellulose, chitosan or any other modified material described in the present Examples. The material is added as a dry powder to a borosilicate glass Pasteur pipette containing a cotton plug pushed to the bottom, clamped to a ring-stand. A few drops of a solution of $I_2$ dissolved in DCM is added. As shown in FIG. 19A-D, the purple $I_2$ solution immediately adsorbs to the top layer of the redox material in the column forming a brown layer. The $I_2$ is being reduced to I–, forming $I_3$– which forms the brown band on the top layer of the mini-column. Mini-columns made from unmodified materials allow the purple color of the $I_2$ DCM solution to pass directly through to the collecting tube below.

Redox functionality for these materials is illustrated by their ability to sequester gold from a solution of $AuCl_3$. A 100 mL solution of 500 ppm $AuCl_3$ is treated with 1 g of redox modified chitosan. After 12 hours stirring, the concentration of remaining $AuCl_3$ is less than 1 ppm.

The proton NMR characterization (FIG. 15) of the 2,5-dithio-7-azabicyclo[2.2.1]heptane modified polyallylamine, as previously described, shows clearly that the primary amines are being functionalized as expected. Peaks at 5.1, 3.3 and 3.1 ppm are very indicative of the bicyclic structure.

Example 22—Industries and Applications

The presently disclosed redox materials can be shown to be extremely efficient at adsorbing gold in the form of Au3+ from aqueous solution. Two grams of the redox active material is stirred in 100 mL of an aqueous solution of 500 ppm gold chloride for 24 hours. At the end of this time, the aqueous solution has gone clear, the redox material has gone reddish-purple, and the concentration of gold in the aqueous solution has dropped to 0 ppm.

For example, 99% of the gold that has been leached from a gold foil with the action of sodium thiosulfate is adsorbed onto the redox material made from chitosan in 20 minutes at pH 2.7.

For example, 99% of the gold that has been leached from e-waste with the action of sodium thiosulfate is adsorbed onto the redox material made from chitosan in 20 minutes at pH 2.7. The chitosan, containing gold as gold nanoparticles, is recovered by filtration.

The presently disclosed redox materials can be shown to be extremely efficient at adsorbing copper in the form of $Cu2+$ from aqueous solutions. Two grams of the redox active material is stirred in 100 mL of an aqueous solution of 500 ppm copper sulfate for 24 hours. At the end of this time, the aqueous solution has gone clear, the redox material has become brown, and the concentration of copper in the aqueous solution has dropped to 0 ppm.

For example, any form of the redox material can be used as a halogen scavenger for use after iodo- or bromo-cyclizations, as an alternative to washing with sodium bisulfite or other suitable reducing reagent in a separatory funnel. A column of convenient size is packed with the redox active material, the crude reaction mixture is 'filtered' through the column, with excess I2 being reduced and transformed to I3− and adsorbing to the top of the column. The colorless reaction mixture is collected at the bottom, and the product isolated as normal.

An important additional application of this disclosure pertains to reaction of the redox active material with chlorine gas. The chlorine gas is bubbled through a stirred aqueous suspension of 1 gram of redox active cellulose. The material is collected by filtration and dried under vacuum. The material does not change its appearance significantly, except that it is now electrostatically charged. This new, reduced material, no longer gives a positive I2 test with DCM, indicating that the 2,5-dithio-7-azabicyclo-[2.2.1]heptane has been oxidized, and now contains a positive charge.

These redox active materials may be used as water filtration agents: filtering excess chlorine from drinking water, removing dissolved toxic metals such as copper and mercury.

These redox active materials have applications as filter agents for air filtration. Removal of mercury, and other airborne toxic metals from industrial operations.

These redox active materials have applications in gold mining. The materials can act as an adsorbing resin for reducing the Au3+ in solution to Au atoms, which spontaneously start to aggregate and form gold nanoparticles tightly bound to the material. This material can be burnt off leaving the gold behind.

Another application is in cyanide-free gold mining. The material can be used in a process employing sodium thiosulfate as the lixiviant in the leaching process in place of cyanide. The redox material then adsorbs 99% of the gold in solution. The solid material is recovered by filtration and the gold is recovered from it by any of a variety of processes.

These redox materials have applications in the medical dialysis field, especially in emergency situations where a patient has been exposed to a high concentration of a toxic metal.

The chitosan, cellulose and, colloidal silica, silica gel bound gold nanoparticles have applications in organic synthesis for a variety of gold-nanoparticle catalyzed reactions for pharmacological applications—drug synthesis.

Since it has been shown that biological material such as amino acids, peptides, proteins and other polymers can be functionalised with at least one of the 2,5-dithio-7-azabicylo[2.2.1]heptane unit of the present disclosure,

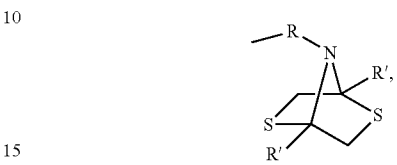

optionally 2,5-dihydroxy-1,4-dithiane, and that one or more atoms of

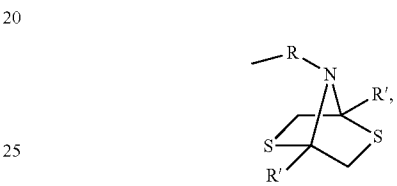

can be replaced with a distinct isotope, the functionalized biological material can be recognised by mass spectrometry based on distinct mass of the functionalized amino acids, peptides, proteins, or polymers due to the isotopes used. Accordingly, when the functionalized biological material is a biomarker for a disease or condition, the 2,5-dithio-7-azabicylo[2.2.1]heptane unit of the present disclosure,

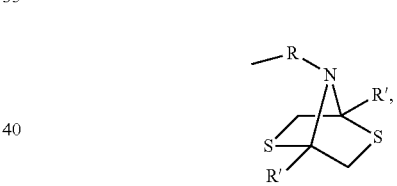

optionally 2,5-dihydroxy-1,4-dithiane, can be used in the diagnosis of the disease or condition. Additionally, when the amino acids, peptides, proteins or polymers are biomarkers for a disease or condition, the functionalized amino acids, peptides, proteins or polymers can be used in the diagnosis of the disease or condition by mass spectrometry. For example, different biological material such as amino acids, peptides, proteins or polymers can be functionalized with different isotopic variants of the 2,5-dithio-7-azabicylo[2.2.1]heptane unit of the present disclosure,

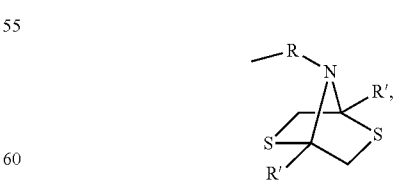
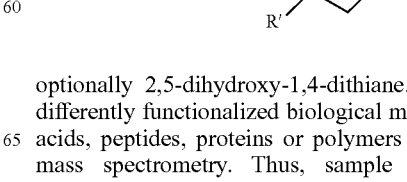

optionally 2,5-dihydroxy-1,4-dithiane. In which case, the differently functionalized biological material such as amino acids, peptides, proteins or polymers can be separated by mass spectrometry. Thus, sample throughput can be increased.

All previously described applications apply to the adsorption of metals in general, toxic or otherwise. For which the resulting material plus metal combination may be used for any the purposes described above.

All publications, patents and patent applications are herein incorporated by reference in their entirety to the same extent as if each individual publication, patent or patent application was specifically and individually indicated to be incorporated by reference in its entirety.

REFERENCES

1. F. Fu, Q Wang, Journal of Environmental Management 92 (2011) 407-418
2. M. A. Alkhabbaz et al./Fuel 121 (2014) 79-85
3. S. Ramsaywack et.al. J. Phys. Chem. C 2012, 116, 7886-7896
4. A. Goswami, A. K. Singh/Analytica Chimica Acta 454 (2002) 229-240

The invention claimed is:

1. A compound of formula:

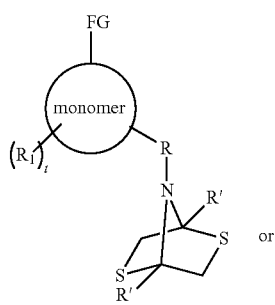

or

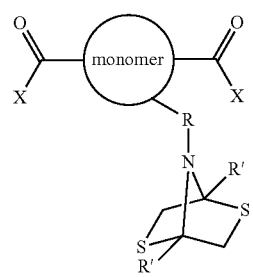

wherein

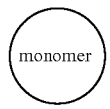

is chosen from $C_1$-$C_{20}$ alkyl, $C_3$-$C_8$ cycloalkyl, $C_6$-$C_{12}$ aryl, $C_1$-$C_{12}$ heteroaryl, $C_1$-$C_{12}$ heterocyclyl and $C_6$-$C_{20}$ aralkyl, and wherein R is a linker or a chemical bond; R' is chosen from hydrogen, $C_1$-$C_{20}$ alkyl, $C_3$-$C_8$ cycloalkyl, $C_6$-$C_{12}$ aryl, $C_1$-$C_{12}$ heteroaryl, $C_1$-$C_{12}$ heterocyclyl and $C_6$-$C_{20}$ aralkyl; $R_1$ is chosen from hydrogen, $C_1$-$C_{20}$ alkyl, $C_3$-$C_8$ cycloalkyl, $C_1$-$C_{12}$ heteroaryl, $C_1$-$C_{12}$ heterocyclyl and $C_6$-$C_{20}$ aralkyl, and t is an integer from 1 to 4 such that the $R_1$ groups (if more than one) could be the same or different, attached to any position around the ring; FG is vinyl, and X is hydroxy, methoxy, ethoxy, 2,2,2-trichloroethoxy or benzyloxy, an enantiomer thereof, a mixture of said compound of said formula and said enantiomer, a diastereoisomer thereof, a stereoisomer thereof or an epimer thereof.

2. The compound of claim 1, wherein the compound is of formula XVII and $R_1$ is chosen from hydrogen and $C_1$-$C_{20}$ alkyl.

3. The compound of claim 1, wherein the compound is of formula XVII and t is 4.

4. The compound of claim 1, wherein the compound is of formula XVII and R is a linker.

5. The compound of claim 1, wherein the compound is of formula XVII and R is a chemical bond.

6. The compound of claim 1, wherein the compound is of formula XVIII and R is a linker.

7. The compound of claim 1, wherein the compound is of formula XVIII and R is a chemical bond.

8. The compound of claim 1, wherein the compound is of formula XVIII and X is hydroxy or methoxy.

9. The compound of claim 1, wherein the compound is of formula II

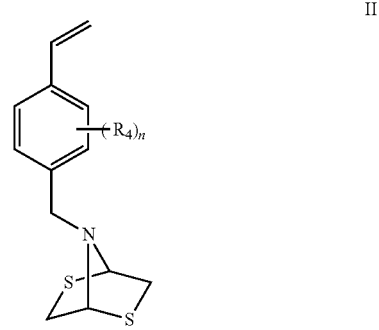

wherein $R_4$ is chosen from hydrogen and $C_1$-$C_{20}$ alkyl, and wherein n is an integer from 1 to 4.

10. The compound of claim 1, wherein the compound is of formula III

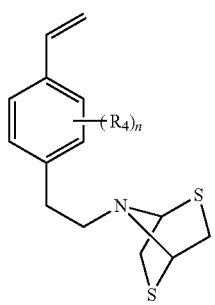

wherein $R_4$ is chosen from hydrogen and $C_1$-$C_{20}$ alkyl, and wherein n is an integer from 1 to 4.

11. The compound of claim 1, wherein the compound is of formula VII
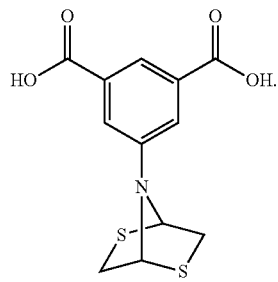
VII
12. The compound of claim 1, wherein the compound is of formula VIII
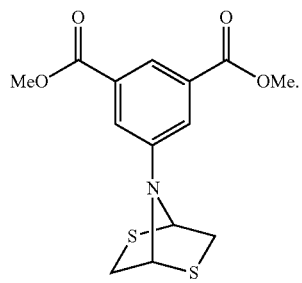
VIII
13. The compound of claim 1, wherein the compound is of formula XI
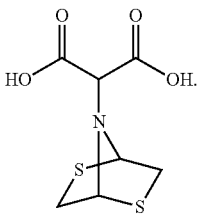
XI
14. The compound of claim 1, wherein the compound is of formula XII
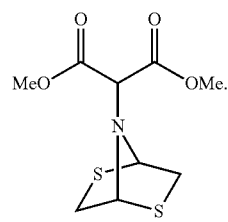
XII
* * * * *